(12) United States Patent
Sankaranarayanapillai et al.

(10) Patent No.: US 10,138,193 B2
(45) Date of Patent: Nov. 27, 2018

(54) METHODS FOR PRODUCING FUELS, GASOLINE ADDITIVES, AND LUBRICANTS USING AMINE CATALYSTS

(71) Applicants: The Regents of the University of California, Oakland, CA (US); BP Corporation North America Inc., Houston, TX (US)

(72) Inventors: Shylesh Sankaranarayanapillai, Albany, CA (US); Sanil Sreekumar, Midland, MI (US); F. Dean Toste, Piedmont, CA (US); Alexis T. Bell, Oakland, CA (US); Amit A. Gokhale, Scotch Plains, NJ (US); Adam Grippo, Oakland, CA (US); George E. Arab, Berkeley, CA (US)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 37 days.

(21) Appl. No.: 15/522,251

(22) PCT Filed: Oct. 28, 2015

(86) PCT No.: PCT/US2015/057893
§ 371 (c)(1),
(2) Date: Apr. 26, 2017

(87) PCT Pub. No.: WO2016/069797
PCT Pub. Date: May 6, 2016

(65) Prior Publication Data
US 2017/0327448 A1 Nov. 16, 2017

Related U.S. Application Data

(60) Provisional application No. 62/072,377, filed on Oct. 29, 2014.

(51) Int. Cl.
C07C 45/74 (2006.01)
B01J 31/02 (2006.01)
(Continued)

(52) U.S. Cl.
CPC ............ *C07C 45/74* (2013.01); *B01J 31/0201* (2013.01); *B01J 31/0204* (2013.01);
(Continued)

(58) Field of Classification Search
None
See application file for complete search history.

(56) References Cited

U.S. PATENT DOCUMENTS 2,434,631 A 1/1948 Winkler et al.
3,781,307 A 12/1973 Chabardes et al.
(Continued)

FOREIGN PATENT DOCUMENTS

CN 101440381 A 5/2009
CN 101787378 A 7/2010
(Continued)

OTHER PUBLICATIONS

Patel et al., Journal of Molecular Catalysis: A Chemical 286(1-2):31-40 • May 2008 (Year: 2008).*
(Continued)

*Primary Examiner* — Karl J Puttlitz
(74) *Attorney, Agent, or Firm* — Morrison & Foerster LLP

(57) ABSTRACT

Provided herein are methods for producing α,β-unsaturated ketones from the condensation of methyl ketones in the presence of an amine catalyst. Such amine catalysts may be supported, for example, on a silica-alumina support. Such amine catalysts may be used in the presence of an additional acid. The α,β-unsaturated ketones may be produced by dimerization and/or timerization of the methyl ketones. Such
(Continued)

α,β-unsaturated ketones may be suitable for use in producing fuels, gasoline additives, and/or lubricants, or precursors thereof. The methyl ketones may be obtained from renewable sources, such as by the fermentation of biomass.

24 Claims, 9 Drawing Sheets

(51) Int. Cl.
    *C10L 1/02*     (2006.01)
    *C10G 3/00*     (2006.01)
    *B01J 31/04*     (2006.01)
    *C07C 1/207*     (2006.01)
    *C07C 49/203*     (2006.01)
    *C10M 105/04*     (2006.01)
    *C12P 7/26*     (2006.01)

(52) U.S. Cl.
    CPC ....... *B01J 31/0222* (2013.01); *B01J 31/0225* (2013.01); *B01J 31/0237* (2013.01); *B01J 31/0238* (2013.01); *B01J 31/0244* (2013.01); *B01J 31/0251* (2013.01); *B01J 31/0254* (2013.01); *B01J 31/0259* (2013.01); *B01J 31/0271* (2013.01); *B01J 31/04* (2013.01); *C07C 1/2076* (2013.01); *C07C 49/203* (2013.01); *C10G 3/50* (2013.01); *C10L 1/02* (2013.01); *C10M 105/04* (2013.01); *C12P 7/26* (2013.01); *B01J 2231/342* (2013.01); *C10M 2203/022* (2013.01); *Y02P 30/20* (2015.11)

(56) References Cited

U.S. PATENT DOCUMENTS

| | | |
|---|---|---|
| 4,250,259 A | 2/1981 | Hou et al. |
| 7,671,246 B2 | 3/2010 | Dumesic et al. |
| 8,075,642 B2 | 12/2011 | Dumesic et al. |
| 2001/0003784 A1 | 6/2001 | Kramer et al. |
| 2005/0089979 A1 | 4/2005 | Ezeji et al. |
| 2007/0244328 A1 | 10/2007 | Wang et al. |
| 2007/0275447 A1 | 11/2007 | Lewis et al. |
| 2008/0015395 A1 | 1/2008 | D'Amore et al. |
| 2008/0015397 A1 | 1/2008 | D'Amore et al. |
| 2008/0103337 A1 | 5/2008 | D'Amore et al. |
| 2008/0132730 A1 | 6/2008 | Manzer et al. |
| 2008/0244961 A1 | 10/2008 | Rusek et al. |
| 2008/0248540 A1 | 10/2008 | Yang |
| 2009/0030239 A1 | 1/2009 | D'Amore et al. |
| 2009/0036716 A1 | 2/2009 | D'Amore et al. |
| 2010/0076233 A1 | 3/2010 | Cortright et al. |
| 2010/0077655 A1 | 4/2010 | Bauldreay et al. |
| 2010/0204526 A1 | 8/2010 | Kouba et al. |
| 2010/0263265 A1 | 10/2010 | Delfort et al. |
| 2010/0268005 A1 | 10/2010 | Rusek et al. |
| 2010/0330633 A1 | 12/2010 | Walther et al. |
| 2011/0172475 A1 | 7/2011 | Peters et al. |
| 2011/0237833 A1 | 9/2011 | Koltermann et al. |
| 2011/0306801 A1 | 12/2011 | Schucker |
| 2012/0059205 A1 | 3/2012 | Rusek |
| 2014/0137465 A1 | 5/2014 | Toste et al. |

FOREIGN PATENT DOCUMENTS

| | | |
|---|---|---|
| CN | 102019177 A | 4/2011 |
| CN | 102188967 A | 9/2011 |
| CN | 102389829 A | 3/2012 |
| CN | 102600827 A | 7/2012 |
| DE | 2257675 | 5/1974 |
| EP | 0444460 A2 | 9/1991 |
| EP | 0719751 A1 | 7/1996 |
| EP | 0828558 B1 | 12/2001 |
| GB | 400384 | 10/1933 |
| GB | 723280 | 2/1955 |
| WO | 1997/19905 A1 | 6/1997 |
| WO | 1998/51813 A1 | 11/1998 |
| WO | 2007/149397 A2 | 12/2007 |
| WO | 2008/066579 A1 | 6/2008 |
| WO | 2008/066581 A1 | 6/2008 |
| WO | 2008/109877 A1 | 9/2008 |
| WO | 2008/111941 A2 | 9/2008 |
| WO | 2008/156320 A1 | 12/2008 |
| WO | 2009/152495 A2 | 12/2009 |
| WO | 2010/098694 A2 | 9/2010 |
| WO | 2011/077242 A1 | 6/2011 |
| WO | 2011/143392 A1 | 11/2011 |
| WO | 2012/001416 A1 | 1/2012 |
| WO | 2012/001417 A1 | 1/2012 |
| WO | 2012/166267 A2 | 12/2012 |
| WO | 2012/166267 A3 | 4/2013 |
| WO | 2014/176552 A2 | 10/2014 |

OTHER PUBLICATIONS

Alonso et al., "Catalytic Conversion of Biomass to Biofuels", Green Chemistry, vol. 12, 2010, pp. 1493-1513.

Alonso et al., "The α-Alkylation of Methyl Ketones with Primary Alcohols Promoted by Nickel Nanoparticles under Mild and Ligandless Conditions", Synlett, No. 12, 2007, pp. 1877-1880.

Ayame et al., "Alumina Solid Lewis Superacid: Activated Benzene and Isomerization of Alkanes on Aluminas Chlorinated at High Temperature", Journal of the Chemical Society, Chemical Communications, 1989, pp. 645-646.

Das et al., "Influence of the Metal Function in the "One-Pot" Synthesis of 4-Methyl-2-Pentanone (Methyl Isobutyl Ketone) from Acetone over Palladium Supported on Mg(Al)O Mixed Oxides Catalysts", Catalysis Letters, vol. 71, No. 3-4, 2001, pp. 181-185.

Debecker et al., "Exploring, Tuning and Exploiting the Basicity of Hydrotalcites for Applications in Heterogeneous Catalysis", Chemistry—A European Journal, vol. 15, 2009, pp. 3920-3935.

Demirbas, A. "The Importance of Bioethanol and Biodiesel from Biomass", Energy Sources, Part B, vol. 3, 2008, pp. 177-185.

Ekeley et al., "The Condensation Products of Diethyl Ketone", Journal of the American Chemical Society, vol. 46, 1924, pp. 446-450.

Goulas et al., "Synergistic Effects in Bimetallic Palladium-Copper Catalysts Improve Selectivity in Oxygenate Coupling Reactions", Journal of the American Chemical Society, vol. 138, 2016, pp. 6805-6812.

Hamid et al., "Borrowing Hydrogen in the Activation of Alcohols", Advanced Synthesis & Catalysis, vol. 349, 2007, pp. 1555-1575.

He et al., "One-Step Synthesis of 2-Pentanone from Ethanol over K—Pd/MnO$_x$—ZrO$_2$—ZnO Catalyst", Journal of Molecular Catalysis A: Chemical, vol. 226, 2005, pp. 89-92.

Hermann, Schlenk, "Beitrag Zur Kenntnis Der Polyen-diketone", Jahrg, vol. 81, 1948, pp. 175-178. (See Communication under 37 CFR § 1.98(a) (3)).

Stetter et al., "Addition Von Aldehyden an Aktivierte Doppelbindungen, XIX. Darstellung Von Ungesattigten 1,4-Diketonen", Chemische Berichte, vol. 112, 1979, pp. 84-94. (See Communication under 37 CFR § 1.98(a) (3)).

Hong-Qing et al., "Preparation and Characterization of Amine Grafted SBA-15 Catalysts and their Application in Aldol Condensation Reaction", Chemistry and Industry of Forest Product, vol. 34, No. 2, Apr. 2014, pp. 1-8 (English Abstract Submitted).

International Preliminary Report on Patentability received for PCT Application No. PCT/US2015/022086, dated Oct. 6, 2016, 9 pages.

International Preliminary Report on Patentability received for PCT Patent Application No. PCT/US2012/035306, dated Dec. 12, 2013, 11 pages.

International Preliminary Report on Patentability received for PCT Patent Application No. PCT/US2014/040760, dated Dec. 17, 2015, 13 pages.

International Preliminary Report on Patentability received for PCT Patent Application No. PCT/US2015/057893, dated May 11, 2017, 8 pages.

(56) References Cited

OTHER PUBLICATIONS

International Preliminary Report on Patentability received for PCT Patent Application No. PCT/US2014/035545, dated Nov. 5, 2015, 13 pages.
International Search Report and Written Opinion received for PCT Patent Application No. PCT/US2012/035306, dated Feb. 13, 2013, 16 pages.
International Search Report and Written Opinion received for PCT Patent Application No. PCT/US2014/035545, dated Nov. 24, 2014, 18 pages.
International Search Report and Written Opinion received for PCT Patent Application No. PCT/US2014/040760, dated Nov. 25, 2014, 19 pages.
International Search Report and Written Opinion received for PCT Patent Application No. PCT/US2015/022086, dated Sep. 29, 2015, 14 pages.
International Search Report and Written Opinion received for PCT Patent Application No. PCT/US2015/057901, dated Feb. 4, 2016, 11 pages.
International Preliminary Report on Patentability received for PCT Patent Application No. PCT/US2015/057901 dated May 11, 2017, 8 pages.
Iuchi et al., "Synthesis of ω-Hydroxy Carboxylic Acids and α, ω-Dimethyl Ketones Using α, ω-Diols As Alkylating Agents", The Journal of Organic Chemistry, vol. 75, No. 5, 2010, pp. 1803-1806.
Kim et al., "Recyclable Gold Nanoparticle Catalyst for the Aerobic Alcohol Oxidation and C—C Bond Forming Reaction between Primary Alcohols and Ketones under Ambient Conditions", Tetrahedron, vol. 65, 2009, pp. 1461-1466.
Kretchmer et al., "A New Furan Synthesis", The Journal of Organic Chemistry, vol. 43, No. 24, 1978, pp. 4596-4598.
Kwon et al., "Recyclable Palladium Catalyst for Highly Selective α Alkylation of Ketones with Alcohols", Angewandte Chemie, vol. 44, 2005, pp. 6913-6915.
Margelefsky et al., "Cooperative Catalysis by Silica-Supported Organic Functional Groups", Chemical Society Reviews, vol. 37, 2008, pp. 1118-1126.
Motokura et al., "Acid-Base Bifunctional Catalysis of Silica-Alumina-Supported Organic Amines for Carbon-Carbon Bond-Forming Reactions", Chem. Eur. J., vol. 14, 2008, pp. 4017-4027.
Motokura et al., "Bifunctional Heterogeneous Catalysis of Silica-Alumina-Supported Tertiary Amines with Controlled Acid-Base Interactions for Efficient 1, 4-Addition Reactions", Chem. Eur. J., vol. 15, 2009, pp. 10871-10879.
Motokura et al., "Heterogeneous Organic Base-Catalyzed Reactions Enhanced by Acid Supports", Journal of the American Chemical Society, vol. 129, 2007, pp. 9540-9541.
Nakatsu et al., "A convenient Synthesis of Olefins Via Deacylation Reaction", Tetrahedron, vol. 60, 2004, pp. 2337-2349.
Non Final Office Action Received for U.S. Appl. No. 14/786,153, dated Feb. 17, 2017, 10 Pages.
Non-Final Office Action received for U.S. Appl. No. 14/123,064, dated Jan. 4, 2016, 10 pages.
Non-Final Office Action received for U.S. Appl. No. 14/123,064, dated Jan. 31, 2017, 9 pages.
Non-Final Office Action received for U.S. Appl. No. 14/123,064, dated Jul. 15, 2016, 10 pages.
Non-Final Office Action received for U.S. Appl. No. 14/895,851, dated Dec. 12, 2016, 23 pages.
Notice of Allowance received for U.S. Appl. No. 14/895,851, dated Apr. 21, 2017, 8 pages.
Qiu et al., "Synthesis and Evaluation of Curcumin Analogues as Potential Thioredoxin Reductase Inhibitors", Bioorganic & Medicinal Chemistry, vol. 16, 2008, pp. 8035-8041.
Requirement for Restriction/Election received for U.S. Appl. No. 14/786,153, dated Aug. 30, 2016, 10 pages.
Roffler et al., "Design and Mathematical Description of Differential Contactors Used in Extractive Fermentations", Biotechnology and Bioengineering, vol. 32, 1988, pp. 192-204.
Roffler et al., "In Situ Extractive Fermentation of Acetone and Butanol", Biotechnology and Bioengineering, vol. 31, 1988, pp. 135-143.
Roffler et al., "In-Situ Recovery of Butanol during Fermentation", Bioprocess Engineering, Part 1: Batch extractive fermentation, vol. 2, Springer-Verlag, 1987, pp. 1-12.
Roffler et al., "In-Situ Recovery of Butanol during Fermentation", Bioprocess Engineering, Part 2: Fed-batch extractive fermentation, vol. 2, Springer-Verlag, 1987, pp. 181-190.
Seebald et al., "Reactions on Alumli.na Oxides, 2nd Notice.: Reactions of butan-2-one on aluminum oxide", Arch. Pharmaz., vol. 305, No. 10, 1972, 18 pages (9 pages of English Translation and 9 pages of Official Copy).
Shimizu et al., "Direct C—C Cross-Coupling of Secondary and Primary Alcohols Catalyzed by a γ-Aiumina-Supported Silver Subnanocluster", Angewandte Chemie International ed. in English, vol. 48, 2009, pp. 3982-3986.
Shimizu et al., "Direct C—C Cross-Coupling of Secondary and Primary Alcohols Catalyzed by a γ-Alumina-Supported Silver Subnanocluster", Angewandte Chemie, vol. 121, 2009, pp. 4042-4046.
Shuikin et al., "Activity of Copper-and Iron-Containing Catalysts in the Reaction of Isophorone with Ammonia and Hydrogen", Petroleum Chemistry, vol. 36, No. 1, 1996, pp. 174-179.
Snell, Rayan William, "Carbon-Carbon Bond Forming Reactions for Bio-Oil Upgrading: Heterogeneous Catalyst and Model Compound Studies", Digital Repository Iowa State University, 2012, 179 pages.
Tan et al., "Advances in Catalysts of Aldol Condensation", Chemical Industry and Engineering, vol. 23, No. 1, Jan. 2006, pp. 70-74 (English Abstract Submitted).
Yamada et al., "A Solid-Phase Self-Organized Catalyst of Nanopalladium with Main-Chain Viologen Polymers: α-Alkylation of Ketones with Primary Alcohols", Organic Letters, vol. 8, No. 7, 2006, pp. 1375-1378.
Yamada et al., "Development of a Convoluted Polymeric Nanopalladium Catalyst: α-Alkylation of Ketones and Ring-Opening Alkylation of Cyclic 1,3-Diketones with Primary Alcohols", Tetrahedron, vol. 63, 2007, pp. 8492-8498.
Final Office Action received for U.S. Appl. No. 15/522,269, dated Apr. 19, 2018, 5 pages.
Notice of Allowance received for U.S. Appl. No. 15/522,269, dated Jun. 28, 2018, 7 pages.
Non-Final Office Action received for U.S. Appl. No. 15/522,269, dated Nov. 16, 2017, 7 pages.
International Search Report and Written Opinion received for PCT Patent Application No. PCT/US2015/057893, dated Jan. 29, 2016, 11 pages.
Patel et al,"Synthetic Talc as a Solid Base Catalyst for Condensation of Aldehydes and Ketones", Journal of Molecular Catalysis A: Chemical, vol. 286, 2008 , pp. 31-40.

* cited by examiner

METHODS FOR PRODUCING FUELS, GASOLINE ADDITIVES, AND LUBRICANTS USING AMINE CATALYSTS

CROSS-REFERENCE TO RELATED APPLICATIONS

This application is a U.S. national stage application of PCT/US2015/057893, filed internationally on Oct. 28, 2015, which claims priority to U.S. Provisional Patent Application No. 62/072,377, filed Oct. 29, 2014, which are incorporated herein by reference in their entireties.

FIELD

The present disclosure generally relates to the production of ketones, and more specifically to the condensation of methyl ketones in the presence of an amine catalyst to produce α,β-unsaturated ketones that are suitable for use as precursors for fuels, gasoline additives, and/or lubricants, and precursors thereof.

BACKGROUND

Transformation of biomass to liquid fuel is desirable to meet the growing demand for transportation fuels in the current diminishing fossil fuel circumstances. As the world's accessible fossil reservoirs are gradually depleted, it is crucial to develop sustainable, long-term strategies based on the utilization of renewable feed stocks. Biomass-derived molecules are inherently oxygen-rich; consequently, the excess oxygen must be removed in order to raise the energy density of the products and make them suitable for transportation fuels.

Some of the main challenges in current transformations of biomass to liquid fuel include sensitivity of such transformations to the concentration of water, and decreases in product yield as the concentration of water present increases. This requires the application of costly additional steps to achieve the desired yield, including the removal of water from reactant fermentation mixtures through distillation and controlling the water content during the reaction. The catalysts used also often have a limited lifetime, requiring high initial catalyst loading or the addition of more catalyst during the reaction.

Thus, what is needed in the art is an alternative process for producing fuels (e.g., gasoline or diesel), gasoline additives, and/or lubricants from biomass.

BRIEF SUMMARY

The present disclosure addresses this need in the art by providing methods for producing α,β-unsaturated ketones using the amine catalysts described herein. The α,β-unsaturated ketones produced from the condensation of methyl ketones may be acyclic products formed by dimerization of the methyl ketones, or cyclic products formed by trimerization of the methyl ketones. The α,β-unsaturated ketone products may be used as precursors for fuels, gasoline additives, and/or lubricants. For example, in one embodiment, the α,β-unsaturated ketones are converted into alkanes for use as fuels, gasoline additives, and/or lubricants.

In one aspect, provided is a method of producing an α,β-unsaturated ketone (or a mixture of such ketones), by contacting a methyl ketone with an amine catalyst and producing an α,β-unsaturated ketone from at least a portion of the methyl ketone by a condensation reaction. In some embodiments, the methyl ketone is a compound of Formula (A):

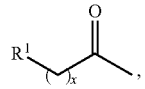
(A)

wherein:
  $R^1$ is H, alkyl, carbocyclyl, or heterocyclyl;
    wherein the alkyl, carbocyclyl, or heterocyclyl is unsubstituted or substituted with one or more substituents independently selected from hydroxyl, nitro, and halo; and
  x is an integer greater than or equal to 1.

In some embodiments, the α,β-unsaturated ketone produced is a compound of Formula (L):

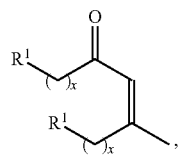
(L)

or any isomers thereof, wherein $R^1$ and x are as defined for Formula (A).

In other embodiments, α,β-unsaturated cyclic ketone produced is of Formula (I), (II), (III), or (IV), or any isomers thereof, or any combinations of the foregoing, wherein:
  the α,β-unsaturated cyclic ketone of Formula (I) is:

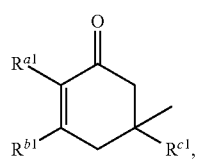
(I)

or any isomers thereof, wherein:
  $R^{a1}$ is $-(CH_2)_{x-1}R^1$;
  $R^{b1}$ is $-(CH_2)_x R^1$; and
  $R^{c1}$ is $-(CH_2)_x R^1$;
the α,β-unsaturated cyclic ketone of Formula (II) is:

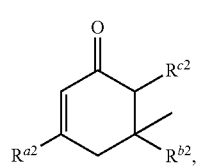
(II)

or any isomers thereof, wherein:
  $R^{a2}$ is $-(CH_2)_x R^1$;
  $R^{b2}$ is $-(CH_2)_x R^1$; and
  $R^{c2}$ is $-(CH_2)_{x-1}R^1$;

the α,β-unsaturated cyclic ketone of Formula (III) is:

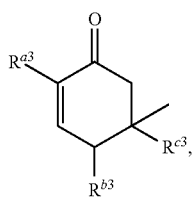

(III)

or any isomers thereof, wherein:
$R^{a3}$ is —$(CH_2)_{x-1}R^1$;
$R^{b3}$ is —$(CH_2)_{x-1}R^1$; and
$R^{c3}$ is —$(CH_2)_x R^1$;
the α,β-unsaturated cyclic ketone of Formula (IV) is:

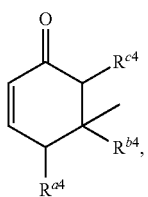

(IV)

or any isomers thereof, wherein:
$R^{a4}$ is —$(CH_2)_{x-1}R^1$;
$R^{b4}$ is —$(CH_2)_x R^1$; and
$R^{c4}$ is —$(CH_2)_{x-1}R^1$;
wherein $R^1$ and x of Formula (L), (I), (II), (III) and (IV) are as defined for Formula (A).

In some variations, provided herein is a method of producing a product mixture of α,β-unsaturated ketones by contacting a methyl ketone having a structure of Formula (A) with any of the amine catalysts described herein, wherein the product mixture includes the α,β-unsaturated ketone of Formula (L), or any isomers thereof, and the α,β-unsaturated cyclic ketone of Formula (I), (II), (III) and/or (IV), or any isomers thereof.

In some variations, the amine catalyst includes an amine moiety having the structure:

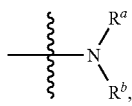

wherein $R^a$ and $R^b$ at each occurrence are independently H, alkyl, carbocyclyl, heterocyclyl, or ether, or any combinations thereof;
wherein the alkyl, carbocyclyl, heterocyclyl, or ether is independently unsubstituted or substituted with one or more substituents selected from alkyl, hydroxyl, amine, oxo, carboxyl, imine, carbocyclyl, heterocyclyl, halo, ether, and thioether;
or $R^a$ and $R^b$ are taken together with the nitrogen atom to which they are both attached to form a heterocycle, wherein the heterocycle is unsubstituted or substituted with one or more substituents selected from alkyl, hydroxyl, amine, oxo, carboxyl, imine, carbocyclyl, heterocyclyl, halo, ether, and thioether.

In other variations, the amine moiety of the amine catalyst includes a heterocycle containing at least one nitrogen atom, wherein the heterocycle is unsubstituted or substituted with one or more substituents selected from alkyl, carbocyclyl, heterocyclyl, carboxyl, hydroxyl, halo, ether, and thioether.

In certain variations, the amine catalyst further includes a solid support and a linker, wherein the linker attaches the amine moiety to the solid support.

In other aspects, provided herein is also a method of producing an α,β-unsaturated ketone by contacting a methyl ketone with any of the amine catalysts described herein, wherein the methyl ketone is contacted with the amine catalyst in the presence of an acid. The acid may supported (e.g., on a solid support) or unsupported.

In other aspects, provided herein is also a ketone or a mixture of ketones produced according to any of the methods described herein. In some variations, the ketone is an α,β-unsaturated ketone having the structure of Formula (L), (I), (II), (III), (IV), or any isomers thereof.

In yet other aspects, provided is a composition that includes a methyl ketone; and any of the amine catalysts described herein. In certain embodiments, the composition further includes water. In some embodiments, the composition further includes any of the α,β-unsaturated ketones described herein.

In yet another aspect, provided is a method of producing an acyclic alkane or cyclic alkane, or a mixture thereof, by:
contacting a methyl ketone with an amine catalyst to produce an acyclic α,β-unsaturated ketone or cyclic α,β-unsaturated ketone, or a mixture thereof; and
hydrodeoxygenating the acyclic ketone or cyclic ketone, or mixtures thereof, to produce the acyclic alkane or cyclic alkane, or a mixture thereof.

In yet another aspect, provided herein is a method of producing an acyclic alcohol or a cyclic alcohol, or a mixture thereof, by:
contacting a methyl ketone with an amine catalyst to produce an acyclic α,β-unsaturated ketone or cyclic α,β-unsaturated ketone, or a mixture thereof; and
reducing (e.g., hydrogenating) the acyclic ketone or cyclic ketone, or a mixture thereof, to produce the acyclic alcohol or cyclic alcohol, or a mixture thereof.

Provided is also a composition that includes:
a fuel (e.g., a diesel fuel), a gasoline additive, or a lubricant, or any mixtures thereof; and
at least one acyclic alkane or cyclic alkane, or at least one acyclic alcohol or cyclic alcohol produced according to any of the methods described above, or any mixtures of the foregoing.

Provided is also a fuel or lubricant, comprising: at least one acyclic alkane or cyclic alkane, or at least one acyclic alcohol or cyclic alcohol produced according to any of the methods described above, or any mixtures of the foregoing.

DESCRIPTION OF THE FIGURES

The present application can be understood by reference to the following description taken in conjunction with the accompanying figures.

DETAILED DESCRIPTION

Figure 1:
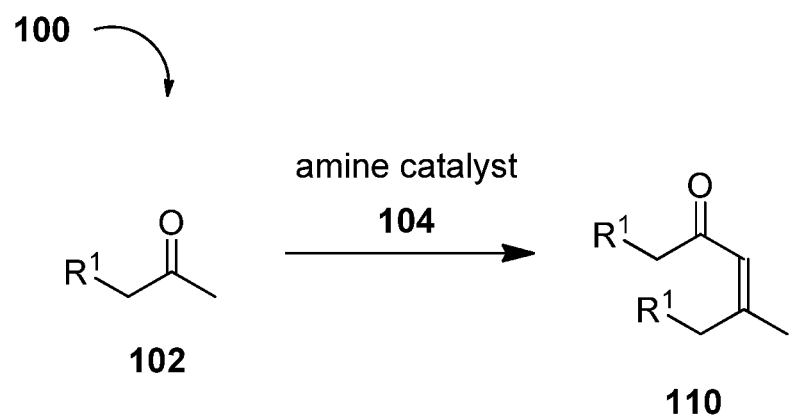
FIG. 1 depicts an exemplary reaction scheme of the dimerization of a methyl ketone in the presence of an amine catalyst.

The following description sets forth numerous exemplary configurations, processes, parameters, and the like. It should be recognized, however, that such description is not intended as a limitation on the scope of the present disclosure, but is instead provided as a description of exemplary embodiments.

In one aspect, provided is a method of producing an α,β-unsaturated ketone by contacting a methyl ketone with an amine catalyst and producing an α,β-unsaturated ketone from at least a portion of the methyl ketone by a condensation reaction.

Provided herein are methods of producing ketones from the condensation of methyl ketones, using a catalytic system having both acidic and basic components. The basic components help to activate nucleophiles, and the acidic components help activate electrophiles to cooperatively catalyze the condensation of the methyl ketones. In the methods described herein, the basic component includes an amine moiety. The basic and acidic components may be provided as part of the amine catalyst, or separately for use with the amine catalyst.

The amine catalyst may be supported or unsupported. In some variations, the amine catalyst is supported, and an additional acid may be optionally provided as part of the solid support and/or separately from the solid support. In other variations, the amine catalyst is unsupported, and an additional acid is provided.

For example, in some variations, the amine catalyst includes at least one amine moiety attached to a solid support. In one variation, the solid support has acidic properties. In another variation, the solid support has non-acidic properties, and the method further includes the use of at least one additional acid to produce ketones. In yet another variation, the solid support has acidic properties, and the method further includes the use of at least one additional acid to produce ketones.

In other variations, the amine catalyst is unsupported, and the method further includes the use of at least one additional acid to produce ketones.

In any of the foregoing variations where acid is added to the reaction mixture, the acid may itself be supported or unsupported.

The ketones produced according to the methods described herein may be suitable for use as precursors for fuels, such as gasoline, jet, and diesel fuels. The methyl ketones used in the methods described herein may be a mixture of methyl ketones obtained from fermentation of biomass.

In one aspect, provided is a method of contacting a methyl ketone with an amine catalyst to produce an α,β-unsaturated ketone from at least a portion of the methyl ketone by a condensation reaction. Such α,β-unsaturated ketones may be cyclic or acyclic. Such α,β-unsaturated may be produced through dimerization or trimerization of the methyl ketone. The α,β-unsaturated ketones may be longer chain ketones. Such produced ketones can be further converted for use as fuels and other products.

As used herein, "α,β-unsaturated ketone" refers to a ketone that has at least one C=C bond between the α-carbon and the β-carbon. The α-carbon is a carbon adjacent to the carbonyl carbon, and the β-carbon is the carbon adjacent to the α-carbon. An α,β-unsaturated ketone may be linear or cyclic, and may have more than one degree of unsaturation. Examples of α,β-unsaturated ketones include, for example, but-3-ene-2-one, pent-3-ene-2-one, hex-4-ene-2-one, and hept-4-ene-2-one, 5-methylhept-4-en-3-one, cyclo-hex-2-enone, and 4,5,5,6-tetramethylcyclohex-2-enone.

In one variation, methyl ketones may dimerize to produce acyclic α,β-unsaturated ketones in the presence of the amine catalysts described herein. In another variation, methyl ketones may trimerize to produce cyclic α,β-unsaturated ketones in the presence of the amine catalysts described herein. In some variations, methyl ketones may produce both dimer products and trimer products in the presence of the amine catalysts described herein.

For example, with reference to FIG. 1, process 100 depicts an exemplary process to produce dimer from methyl ketone 102, wherein $R^1$ is as defined herein for Formula (A). Methyl ketone 102 is contacted with amine catalyst 104 and undergoes a self-condensation reaction to produce the dimer product that is α,β-unsaturated ketone 110. In certain embodiments, process 100 may be varied. For example, in one embodiment the amine catalyst is a supported amine catalyst. In another embodiment the amine catalyst is an unsupported amine catalyst. In another embodiment methyl ketone 102 is contacted with amine catalyst 104 in the additional presence of an acid. In one embodiment, the additional acid is a supported acid. In another embodiment the additional acid is an unsupported acid.

With reference to FIG. 1, it should be generally understood that one or more steps may be omitted or added to process 100. For example, methyl ketone 102 may be contacted with amine catalyst 104 in the further presence of a solvent. In another embodiment, amine catalyst 104 is isolated from the reaction mixture, and then contacted with additional methyl ketone. In yet another embodiment, methyl ketone 102 is contacted with amine catalyst 104 to produce a cyclic α,β-unsaturated ketone trimer product. In certain variations, the cyclic trimer product may be produced in addition to the dimer product 110. In other variations, the cyclic trimer product is produced, and the acyclic dimer product is not produced. In yet other variations, a mixture of cyclic trimer product and acyclic dimer product is produced.

Further, it should generally be understood that a mixture of methyl ketones may be used in the methods described herein, and the resulting products will be a mixture of ketone products.

Such methyl ketones and/or catalysts may be obtained from any commercially available sources, as well as any methods known to one of skill in the art.

The starting materials, the amine catalysts, the acid, the solvent and other reagents, as well as the reaction conditions and products are further described below.

The Amine Catalyst

The amine catalyst used in the methods described here include at least one amine moiety. In some variations, the amine catalyst may be a supported catalyst, and further include a solid support. In other variations, the amine catalyst is unsupported. Any suitable amine-containing catalyst that can catalyze the condensation of methyl ketones may be used herein. Any combinations of the amine catalysts described herein may be used.

Amine Moiety

In some embodiments, the amine catalyst may include a primary amine (e.g., R'—NH$_2$), a secondary amine (e.g., R''R'—NH), or a tertiary amine (e.g., R'''R''R'—N), or any combinations thereof.

In some variations, the amine catalyst includes a moiety having the structure:

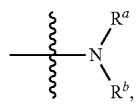

wherein:
$R^a$ and $R^b$ at each occurrence are independently H, alkyl, carbocyclyl, heterocyclyl, or ether, or any combinations thereof;
or $R^a$ and $R^b$ are taken together with the nitrogen atom to which they are both attached to form a heterocycle.

In certain variations, the alkyl, carbocyclyl, heterocyclyl, or ether of $R^a$ and $R^b$ at each occurrence are independently unsubstituted or substituted with one or more substituents selected from alkyl, hydroxyl, amine, oxo, carboxyl, imine, carbocyclyl, heterocyclyl, halo, ether, and thioether. It should be understood that, as used herein, the amine substituent of the amine moiety of the catalyst refers to —NRR', and in some variations, each R and R' is independently H, alkyl, carbocyclyl, or heterocyclyl.

In certain variations, the heterocycle formed when $R^a$ and $R^b$ are taken together is unsubstituted or substituted with one or more substituents selected from alkyl, hydroxyl, amine, oxo, carboxyl, imine, carbocyclyl, heterocyclyl, halo, ether, and thioether.

In some embodiments, either $R^a$ or $R^b$ is H, and the other $R^a$ or $R^b$ is alkyl, carbocyclyl, heterocyclyl, ether, or any combinations thereof. In other embodiments, either $R^a$ or $R^b$ is H, and the other $R^a$ or $R^b$ is alkyl.

In some embodiments, $R^a$ and $R^b$ are independently H, or alkyl. In certain embodiments, $R^a$ is H and $R^b$ is alkyl. In yet other embodiments, $R^a$ and $R^b$ are independently alkyl. In some embodiments, $R^a$ and $R^b$ are independently H, methyl, ethyl, propyl, butyl, pentyl, or hexyl. The alkyl branched or unbranched alkyl. For example, $R^a$ and $R^b$ may be independently H, isopropyl, isobutyl, or tert-butyl.

In some embodiments, $R^a$ and $R^b$ are independently H or alkyl substituted with an amine. In one variation, $R^a$ is H and $R^b$ is

In another variation, $R^a$ is H and $R^b$ is

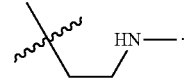 [SMILES: *CCNC]

In other embodiments, $R^a$ and $R^b$ may be taken together with the nitrogen atom to which they are both attached to form a heterocyclyl, wherein the heterocyclyl is unsubstituted or substituted with one or more substituents selected from alkyl, hydroxyl, amine, oxo, carboxyl, imine, carbocyclyl, heterocyclyl, halo, ether, and thioether.

In some embodiments, the amine catalyst includes an unsubstituted or substituted heterocycle. For example, in one embodiment, the amine catalyst includes a pyrrolidinyl moiety or a piperidinyl moiety.

In some embodiments, the amine catalyst includes a heterocyclyl that includes at least one nitrogen atom, wherein the heterocyclyl is unsubstituted or substituted with one or more substituents independently selected from alkyl, carbocyclyl, heterocyclyl, carboxyl, hydroxyl, halo, ether, and thioether. For example, in one embodiment, the amine catalyst includes a proline moiety.

In some embodiments, the amine catalyst includes a heterocycle containing more than one nitrogen atom. For example, in one embodiment, the amine catalyst includes a piperazinyl moiety, an imidazolyl moiety, a triazabicyclodecene moiety, or an aminopyridinyl moiety. In other embodiments, the amine catalyst is piperazine, imidazole, triazabicyclodecene, or aminopyridine.

In some embodiments, the amine catalyst includes an —NH$_2$, methylamine, ethylamine, propylamine, dimethylamine, diethylamine, dipropylamine, ethane 1,2-diamine, or N$^1$-(2-aminoethyl)ethane-1,2-diamine moiety, or any combinations thereof. In other embodiments, the amine catalyst includes an imidazole, pyridine, triazabicyclodecene, pyrrolidine, proline, or 4-dimethylaminopyridine moiety, or any combinations thereof. In certain embodiments, the amine catalyst includes a moiety selected from:

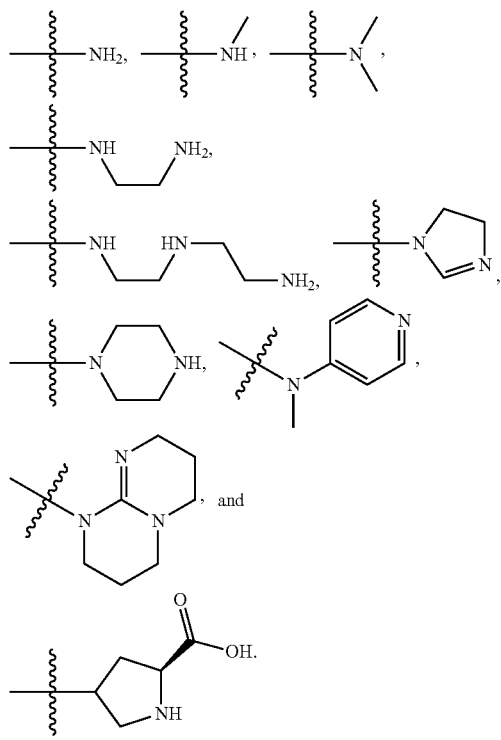

In some variations, the amine catalyst includes:

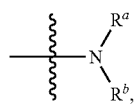

wherein R$^a$ and R$^b$ are independently H or Formula (B):

wherein:
each R$^2$, R$^3$, R$^4$, R$^5$, R$^6$, R$^7$, and R$^8$ are independently H or alkyl; and
f, g, and h are independently integers greater than or equal to one.
In one embodiment of the amine catalyst,
R$^a$ is H;
R$^b$ is a moiety of Formula (B), wherein R$^2$, R$^3$, R$^4$, R$^5$, R$^6$, R$^7$, and R$^8$ of the moiety of Formula (B) are each H; and
f is 2, g is 1, and h is 2.

In one variation of the amine catalyst, R$^a$ is H, and R$^b$ is a moiety of Formula (B), wherein the moiety of Formula (B) is

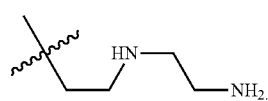

Thus, the amine moiety is

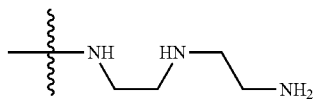

Supported Catalysts

In some embodiments, the amine catalyst is a supported amine catalyst. In certain embodiments, the supported amine catalyst includes an amine moiety attached to a solid support.

In other embodiments, the supported amine catalyst includes a solid support, a linker, and an amine moiety, where the linker attaches the amine moiety to the solid support.

Any suitable methods known in the art to attach the amine moiety to the solid support may be employed. For example, the amine moiety may be attached to the solid support by silylation. An exemplary method to attach an amine moiety to a solid support by silylation is as follows. Silica or silica-alumina supports may be mixed with an organosilane containing an amine moiety, and a solvent. The mixture may then be heated (e.g. at or above 320 K) to modify the support, and the silylated support may be isolated by any method known in the art (e.g. by filtration), optionally washed with solvent, and optionally dried to obtain a support that includes an amine moiety. One of skill in the art would know how to select an appropriate organosilane.

In some embodiments, the solid support is an acidic support. For example, in one variation, the acidic support is silica, alumina, or silica-alumina.

In some variations, the solid support is porous. Examples of suitable porous supports include silica, alumina, silica-alumina, titanium oxides (for example TiO$_2$), zirconium oxides (for example ZrO$_2$), and niobium oxides (for example Nb$_2$O$_5$). In certain variations, the solid support may be a combination of porous and nonporous materials, or may be a material with porous and nonporous regions. In certain variations, the solid support includes silica, alumina, silica-alumina, or any combinations thereof.

In certain embodiments, the solid support is porous having pores with an average diameter between 2 and 50 nm, between 2 and 40 nm, between 2 and 30 nm, or between 2 and 25 nm. In some embodiments, the solid support is porous, wherein all the pores have a diameter between 2 and 50 nm, between 2 and 40 nm, between 2 and 30 nm, or between 2 and 25 nm. In other embodiments, the solid support is porous, wherein at least a portion of the pores have a diameter between 2 and 50 nm, between 2 and 40 nm, between 2 and 30 nm, or between 2 and 25 nm.

In some embodiments, the solid support is mesoporous. In some variations, the entire solid support may be mesoporous, or sections of the solid support may be mesoporous. Mesoporous solids include mesoporous silica, mesoporous alumina, mesoporous silica-alumina, or any combinations thereof. Examples of suitable mesoporous solids include MCM-41, SBA-15, and KIT-6. In some variations, mesoporous solids can also include mesoporous oxides of titanium, zirconium, cerium, tin, niobium, and tantalum, or any combinations thereof. In some embodiments, the solid support may be a combination of nonporous and mesoporous materials, or may be a material with mesoporous and nonporous regions.

In some embodiments, the solid support is an acidic support. It should be understood that an "acidic support" is a support that has acidic properties. In some variations, the acidic support includes at least one Brønsted acid site, at least one Lewis acid site, or a combination thereof. For example, silica-alumina has both Brønsted acid sites and Lewis acid sites. Support acidity may be measured by a variety of techniques known to one of skill in the art. For example, acidity of the support may be measured by monitoring pyridine adsorption onto the support through infrared (IR) spectroscopy.

Modification of the Solid Support

The solid support may be modified to include groups other than the amine moiety. The entire solid support or at least a portion of the solid support may be modified to include groups other than the amine moiety.

For example, the solid support may be modified to include silicon, aluminum, germanium, boron, or phosphorous atoms, or any combinations thereof. In some embodiments, the solid support is silica-alumina modified to include silicon, aluminum, germanium, boron, or phosphorous atoms, or any combinations thereof. In one embodiment, the solid support is silica-alumina modified to include additional silicon atoms. In another embodiment, the solid support is alumina modified to include silicon atoms. In yet another embodiment, the solid support is mesoporous silica modified to include additional silicon atoms.

The solid support may be modified to include acid moieties. For example, the solid support may be modified to include a sulfonic acid moiety, a phosphoric acid moiety, a carboxylic acid moiety, or any combinations thereof. In some embodiments, the solid support is silica-alumina modified to include a phosphoric acid moiety, a carboxylic acid moiety, or a sulfonic acid moiety. Any suitable methods known in the art to modify the solid support of the amine catalyst to include acid moieties may be employed. For example, silica and silica-alumina supports may be modified with organosilane compounds containing acid moieties. An exemplary method to modify a solid support with an organosilane compound containing an acid moiety is as follows. Silica or silica-alumina supports may be mixed with an organosilane containing an acid moiety, and a solvent. The mixture may then be heated (e.g. at or above 320 K) to modify the support, and the modified support may be isolated by any method known in the art (e.g. by filtration), optionally washed with solvent, and optionally dried to obtain a support that has been modified to include an acid moiety. One of skill in the art would recognize how to select an appropriate organosilane.

The solid support may also be modified by silylation. For example, in some variations, the solid support is silica-alumina that has undergone silylation. Any suitable methods known in the art to modify the solid support of the amine catalyst to include silyl moieties may be employed. For example, silica and silica-alumina supports may undergo silylation with organosilane compounds. An exemplary method to prepare a silylated solid support is as follows. Silica or silica-alumina supports may be mixed with an organosilane, and a solvent. The mixture may then be heated (e.g. at or above 320 K) to modify the support, and the modified support may be isolated by any method known in the art (e.g. by filtration), optionally washed with solvent, and optionally dried to obtain a support that has been silylated. One of skill in the art would know how to select an appropriate organosilane (e.g. methyltrimethoxysilane).

The solid support may be modified to include more than one group other than the amine moiety. For example, in some embodiments, the solid support is modified to include a sulfonic acid moiety, and has undergone silylation. In other embodiments, the solid support is modified to include additional silicon atoms, and to include a carboxylic acid moiety. In yet other variations, the solid support is modified to include a phosphoric acid moiety, silicon atoms, and has undergone silylation. In certain variations, the solid support is modified to include a phosphoric acid moiety, a carboxylic acid moiety, silicon atoms, and phosphorous atoms. In one embodiment, the solid support is silica-alumina modified to include additional silicon atoms, and that has undergone silylation. In another embodiment, the solid support is alumina modified to include silicon atoms, and that has undergone silylation.

Any suitable methods known in the art to modify the solid support of the amine catalyst to include more than one group other than the amine moiety may be employed. For example, the solid support may be modified by more than one organosilane compound. An exemplary method to prepare a solid support modified by more than one group other than the amine moiety is as follows. Silica or silica-alumina supports may be mixed with an organosilane containing an acid moiety, and a solvent. The mixture may then be heated (e.g. at or above 320 K) to modify the support, and the modified support may be isolated by any method known in the art (e.g. by filtration), optionally washed with solvent, and optionally dried to obtain a solid support that has been modified to include an acid moiety and additional silicon atoms. One of skill in the art would know how to select an appropriate organosilane.

Linker

The amine catalysts described herein may, in some embodiments, have a linker connecting the solid support and the amine moiety. In one variation, the linker, when present, may include -alkyl-, -aliphatic-, -aryl-, -carbocycle-, -heterocycle-, -sulfone-, or -ether-, or any combinations thereof.

It should be understood that, as used herein, -moiety- refers to a moiety having bivalency. For example, -alkyl- refers to an alkyl moiety with bivalency. For example, "-propyl-" refers to —CH$_2$CH$_2$CH$_2$—, "-butyl-" refers to —CH$_2$CH$_2$CH$_2$CH$_2$—, and "-pentyl-" refers to —CH$_2$CH$_2$CH$_2$CH$_2$CH$_2$—.

Similarly, -ether- refers to an ether moiety with bivalency. For example, "-ethoxyethane-" refers to —CH$_2$CH$_2$OCH$_2$CH$_2$—.

In one embodiment, the linker may be -propyl-, -butyl-, -pentyl-, -hexyl-, -heptyl-, -octyl-, -nonyl-, or -decyl-. In one embodiment, the linker is -propyl-.

The linker may be unsubstituted, or substituted with one or more groups independently selected from alkyl, hydroxyl, amine, oxo, carboxyl, imine, carbocyclyl, and heterocyclyl.

In one variation, the linker may be -ether- substituted with a hydroxyl group. In one variation, the linker is

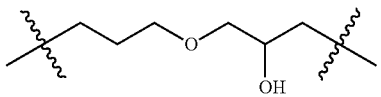

In one embodiment, the linker includes a combination of -alkyl-, -carbocycle-, and -sulfone-. For example, in one embodiment the linker is

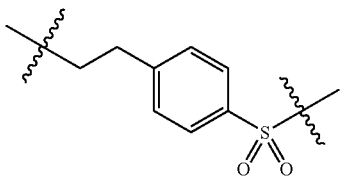

The linker has a certain length between the amine moiety and the solid support. The length of the linker may affect the activity of the supported amine catalyst, and affect product yield. In some embodiments, the linker includes 3, 4, 5, 6, 7, 8, 9, or 10 linear chain atoms. In one embodiment, the linker includes at least 3 linear chain atoms. Linkers with 3 linear chain atoms include

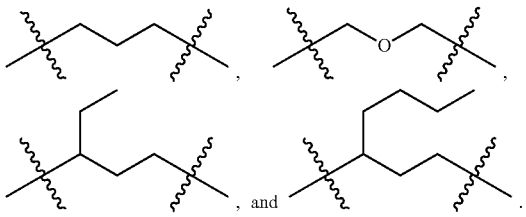

The linker is attached to the solid support. In some embodiments, the linker is attached to the solid support through a C—Si, C—B, C—Ge, or C—P bond. For example, a -propyl- linker may, at one end of the linker, be attached through a C—Si bond to a Si atom on the solid support, while the other end of the linker is attached to the amine moiety. For example, the support may be modified by silylation to include additional Si atoms.

Any suitable methods known in the art to attach the linker to the solid support may be employed. For example, the linker may be attached to the solid support by silylation, wherein the organosilane includes the linker. An exemplary method to attach a linker to a solid support is as follows. Silica or silica-alumina supports may be mixed with an organosilane, and a solvent. The mixture may then be heated (e.g., at or above 320 K) to modify the support, and the modified support may be isolated by any method known in the art (e.g., by filtration), optionally washed with solvent, and optionally dried to obtain a solid support modified to contain a linker, wherein the linker is attached to the solid support through a C—Si bond.

In certain embodiments, the solid support has been modified to contain a Si, B, Ge, or P atom, and the linker is bound to that Si, B, Ge, or P atom. For example, silica-alumina may be modified to contain additional Si atoms, and the linker may be bound to one of those additional Si atoms. Any suitable methods known in the art to modify the solid support of the amine catalyst to include Si, B, Ge, or P atoms may be employed. For example, the support may be modified by silylation to include additional Si atoms. An exemplary method to modify a solid support to include additional Si atoms is as follows. Silica or silica-alumina supports may be mixed with an organosilane, and a solvent. The mixture may then be heated (e.g., at or above 320 K) to modify the support, and the modified support may be isolated by any method known in the art (e.g., by filtration), optionally washed with solvent, and optionally dried to obtain a solid support modified by silylation to include additional Si atoms.

The supported amine catalyst may be used in combination with one or more additional acids. Suitable acids are described in further detail below.

Unsupported Catalysts

In other embodiments, the amine catalyst is an unsupported amine catalyst. An unsupported amine catalyst may include a primary amine (e.g., R'—$NH_2$), a secondary amine (e.g., R"R'—NH), or a tertiary amine (e.g., R'''R"R'—N), or any combinations thereof. For example, in some variations, the unsupported amine catalyst includes a primary amine and a secondary amine. In other variations, the unsupported amine catalyst includes a secondary amine and a tertiary amine. In yet other variations, the unsupported amine catalyst includes two tertiary amines and a secondary amine. In certain variations, the unsupported amine catalyst includes at least one secondary amine.

In some variations, the unsupported amine catalyst is:

wherein:

$R^a$ and $R^b$ at each occurrence are independently H, alkyl, carbocyclyl, heterocyclyl, or ether, or any combinations thereof; or $R^a$ and $R^b$ are taken together with the nitrogen atom to which they are both attached to form a heterocycle; and $R^c$ is independently H, alkyl, carbocyclyl, heterocyclyl, or ether, or any combinations thereof; or $R^a$, $R^b$, and $R^c$ are taken together with the nitrogen atom to which they are all attached to form an unsubstituted or substituted heterocycle.

In certain variations, the alkyl, carbocyclyl, heterocyclyl, or ether of $R^a$, $R^b$ and $R^c$ at each occurrence are independently unsubstituted or substituted with one or more substituents selected from alkyl, hydroxyl, amine, oxo, carboxyl, imine, carbocyclyl, heterocyclyl, halo, ether, and thioether. It should be understood that, as used herein, the amine substituent of the amine moiety of the catalyst refers to —NRR', and in some variations, each R and R' is independently H, alkyl, carbocycle, or heterocycle.

In certain variations, the heterocycle formed when $R^a$ and $R^b$ are taken together, or when $R^a$, $R^b$, and $R^c$ are taken together, is unsubstituted or substituted with one or more substituents selected from alkyl, hydroxyl, amine, oxo, carboxyl, imine, carbocyclyl, heterocyclyl, halo, ether, and thioether.

In some embodiments, one of $R^a$, $R^b$, or $R^c$ is H, and the other two remaining $R^a$, $R^b$, and $R^c$ are independently alkyl, carbocyclyl, heterocyclyl, ether, or any combinations thereof. In other embodiments, one of $R^a$, $R^b$, or $R^c$ is H, and the other two remaining $R^a$, $R^b$, and $R^c$ are independently alkyl.

In some embodiments, $R^a$, $R^b$, and $R^c$ are taken together with the nitrogen atom to which they are all attached to form a heterocycle. For example, in one embodiment, the unsupported amine catalyst is

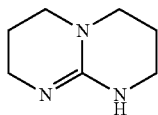

In other embodiments, R$^a$ and R$^b$ are taken together with the nitrogen atom to which they are both attached to form a heterocycle, and R$^c$ may be H, alkyl, or heterocyclyl. For example, in certain variations, the unsupported amine catalyst is

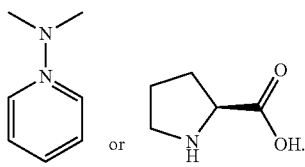

Examples of suitable unsupported amine catalysts include piperazine, pyrrolidine, proline, dimethylamine, diethylamine, dipropylamine, dibutylamine, dipentylamine, N-methylethylamine, N-methylpropan-1-amine, N-ethylpropan-1-amine, N-methylbutan-1-amine, N-ethylbutan-1-amine, or N-propylbutan-1-amine. In certain embodiments, the unsupported amine is piperazine, pyrrolidine, proline, dibutylamine, or N-methylbutan-1-amine. In yet other embodiments, the unsupported amine includes ethane 1,2-diamine, N$^1$-ethylethane-1,2-diamine, or N$^1$-(2-aminoethyl)ethane-1,2-diamine. In other embodiments, the amine catalyst includes imidazole, pyridine, triazabicyclodecene, or 4-dimethylaminopyridine.

When the amine catalyst is unsupported, it is used in combination with at least one additional acid. The additional acid may be a supported or unsupported acid. In certain embodiments, piperazine is used in combination with acetic acid, pyrrolidine is used in combination with acetic acid, pyrrolidine is used in combination with benzoic acid, proline is used in combination with acetic acid, or diethylamine is used in combination with acetic acid.

Properties of the Amine Catalyst

The amine catalysts described herein help to catalyze the condensation of methyl ketones in the presence of water. Water may be present in the reaction mixture for various reasons. For example, water can be produced as a byproduct of the condensation reaction. Water may be present in the starting materials used. For example, in some embodiments, the methyl ketone(s) is/are provided in a fermentation mixture, which can also include water.

Enamine Complex

In some variations, the condensation of methyl ketones catalyzed by the amine catalysts described herein can proceed through an enamine complex, or tautomers thereof. An enamine includes both an alkene and an amine functional group. One generalized structure of an enamine complex is:

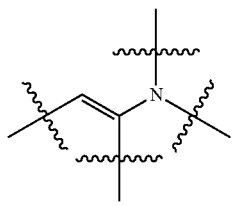

In some variations, the enamine may tautomerize to an imine. An imine includes a C=N bond.

Figure 8:
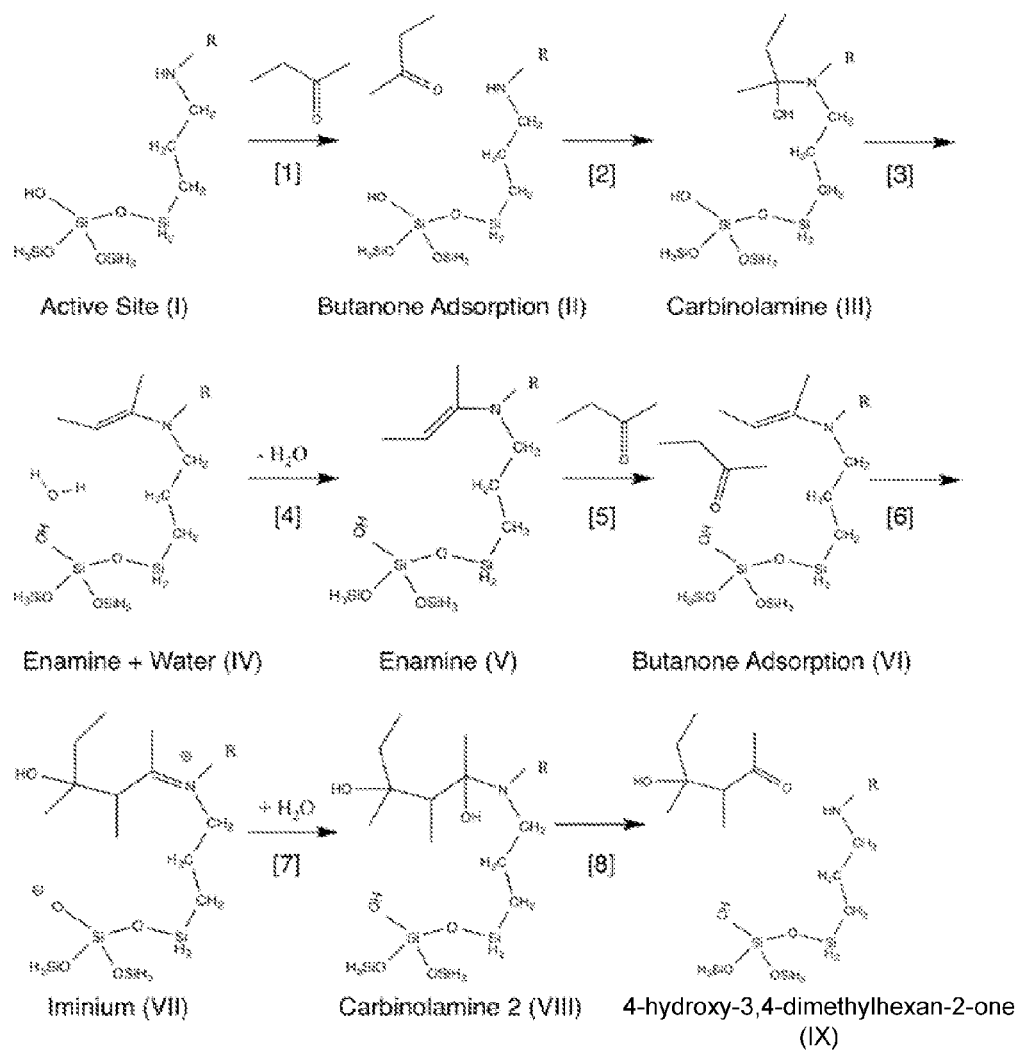
FIG. 8 depicts an exemplary reaction scheme showing one possible reaction mechanism for butan-2-one condensation catalyzed by an amine catalyst.

Without wishing to be bound by any theory, the reaction mechanism of methyl ketone condensation through an enamine complex is provided in FIG. 8, which shows an exemplary reaction mechanism for the condensation of butan-2-one to produce 4-hydroxy-3,4-dimethylhexan-2-one, which undergoes dehydration to produce 3,4-dimethylhex-3-en-2-one and one molecule of water. One molecule of butan-2-one forms a carbinolamine complex with the amine moiety of the catalyst, to produce an enamine complex and a molecule of water. A second butan-2-one molecule is adsorbed to form an imium complex, which includes an imine moiety. Upon the addition of one molecule of water, the iminium complex is transformed into a second carbinolamine complex. The carbinolamine is released from the amine catalyst as 4-hydroxy-3,4-dimethylhexan-2-one, which undergoes dehydration to produce 3,4-dimethylhex-3-en-2-one and one molecule of water.

The condensation of methyl ketones described by this system produce water as a byproduct in addition to the ketone product. Thus, in some embodiments, described herein are methods of producing an α,β-unsaturated ketone by contacting a methyl ketone with an amine catalyst to form an enamine complex, and producing an α,β-unsaturated ketone from the enamine complex. It should generally be understood that a mixture of methyl ketones may also be used in the methods described herein.

In some embodiments, the amount of water present in the reaction mixture is at least 99 wt %, at least 90 wt %, at least 80 wt %, at least 70 wt %, at least 60 wt %, at least 50 wt %, at least 40 wt %, at least 30 wt %, at least 20 wt %, at least 10 wt %, at least 5 wt %, at least 1 wt %, at least 0.1 wt %, or at least 0.01 wt %. In other embodiments, the amount of water present in the reaction mixture is at least 99 wt %, at least 90 wt %, at least 80 wt %, or at least 70 wt %. In some embodiments, the amine catalyst described herein may catalyze the condensation of methyl ketones in the absence of water.

While the condensation reaction may be carried out in the presence of water, in other embodiments, water produced during the reaction may also be controlled or removed. Water produced during the reaction may be controlled or removed using any suitable methods or techniques known in the art. For example, water produced during the reaction may be controlled or removed by distillation (e.g., using a Dean-Stark apparatus) or by the use of a biphasic reaction system.

Additional water may also be present in the reaction mixture from the starting materials (e.g., starting methyl ketone) provided. For example, the methyl ketone(s) may be obtained from a fermentation product mixture, and the fermentation product mixture may additionally contain water. Thus, provided herein is also a method of contacting a composition comprising biomass and/or sugars with a fermentation host to produce a fermentation product mixture, wherein the fermentation product mixture includes methyl ketone(s), and contacting the fermentation product mixture with an amine catalyst as described herein to produce α,β-unsaturated ketone(s) from the condensation of the methyl ketone(s). In some embodiments, the fermentation host is selected from fungi and bacteria.

Catalyst Lifetime

The lifetime of the catalyst used may be described in various ways. In some variations, the lifetime of the amine catalysts may be described based on the yield of ketones produced over a period of time. In certain variations, the lifetime may also be expressed based at a given catalyst loading. In yet other variations, the lifetime of the amine catalyst may be described based on the yield based on the amount of water present in the reaction mixture.

As used herein, the term "yield" refers to the total amount of product expressed in a percentage (%) relative to the amount of methyl ketone reactant present in the starting reaction mixture. For example, where multiple ketone compounds are produced, the overall reaction yield refers to the combined molar yields of the ketone products, calculated with respect to the molar amount of methyl ketone reactant present in the starting reaction mixture.

In certain embodiments, the amine catalyst has less than a 50%, less than a 40%, less than a 30%, less than a 20%, or less than a 10% reduction in yield over a 16 h period. In one embodiment, the amine catalyst has less than a 20% reduction in yield over 16 h.

In certain embodiments, the amine catalyst has less than a 50%, less than a 40%, less than a 30%, less than a 20%, or less than a 10% reduction in yield when water is present at equal to or greater than 0.6 g water per g amine catalyst. In one embodiment, the amine catalyst has less than a 20% reduction in yield when water is present at equal to or greater than 0.6 g water per g catalyst.

In yet other embodiments, the product yield produced from reactants in the presence of the amine catalyst may vary both over time and with the amount of water present. In some embodiments, the amine catalyst has less than a 50%, less than a 40%, less than a 30%, less than a 20%, or less than a 10% reduction in yield when water is present at equal to or greater than 0.6 g water per g amine catalyst. In one embodiment, the amine catalyst has less than a 20% reduction in yield over a 16 h period when water is present at equal to or greater than 0.6 g water per g catalyst.

In some embodiments, the methyl ketone is obtained from a fermentation product mixture, and the fermentation product mixture may additionally contain water. Thus, provided herein is also a method of contacting a composition comprising biomass and/or sugars with a fermentation host to produce a fermentation product mixture, wherein the fermentation product mixture includes a methyl ketone, and contacting the fermentation product mixture with an amine catalyst as described herein to produce an α,β-unsaturated ketone from the condensation of the methyl ketone. In some embodiments, the fermentation host is selected from fungi and bacteria.

In certain embodiments, the product yield produced from reactants in the presence of the amine catalyst varies with the ratio of reactant to catalyst. The ratio may be described with different expressions for different systems, for example weight hour space velocity (WHSV) and liquid hour space velocity (LHSV). As used herein, WHSV refers to the weight of reactant feed per unit weight of the catalyst per hour. As used herein, LHSV refers to the weight of liquid reactant feed per unit weight of the catalyst per hour. One of skill in the art would recognize how to convert the WHSV values into the LHSV, and vice versa.

In some embodiments, a product yield of at least 5%, of at least 10%, of at least 20%, of at least 30%, of at least 40%, or of at least 50% is obtained when the WHSV is about 0.2 $hr^{-1}$. In one embodiment, a product yield of at least 10% is obtained when the WHSV is about 0.2 $hr^{-1}$. In another embodiment, a product yield of at least 10% is obtained when the WHSV is about 0.2 $hr^{-1}$.

In other embodiments, a product yield of at least 5%, of at least 10%, of at least 20%, of at least 30%, of at least 40%, or of at least 50% is obtained when the LHSV is 0.012 $hr^{-1}$.

In one embodiment, a product yield of at least 10% is obtained when the LHSV is 0.012 $hr^{-1}$. In another embodiment, a product yield of at least 10% is obtained when the LHSV is 0.012 $hr^{-1}$.

The Acid

In some embodiments, at least one acid is combined with the amine catalysts described herein to convert the methyl ketone(s) into ketone product(s). The acid may be a supported or unsupported acid. It should be understood that the solid support of the acid and the amine may be the same solid support, or separate solid supports.

In one embodiment, the amine catalyst includes a solid support having acidic properties, and at least one additional acid is optionally used in the methods described herein.

In another embodiment, the amine catalyst is includes a solid support having non-acidic properties, and the amine catalyst is used in combination with at least one acid.

In yet another embodiment, the amine catalyst is an unsupported amine catalyst, and the amine catalyst is combined with one or more acids.

Suitable acids may include organic acids and inorganic acids. Examples of suitable organic acids may include acetic acid, benzoic acid, terephthalic acid, phthalic acid, isophthalic acid, adipic acid, succinic acid, oxalic acid, pimelic acid, valeric acid, muconic acid, mucic acid, toluic acid, and citric acid, or any combinations thereof. Examples of inorganic acids may include hydrochloric acid, nitric acid, sulfuric acid, boric acid, phosphoric acid, or any combinations thereof. Any combination of the acids described herein may be used.

In one variation, the acid is supported. Supported acids include solid supports which contain acidic groups. Examples of supported acids may include alumina, silica, silica-alumina, titanium oxides (for example $TiO_2$), zirconium oxides (for example $ZrO_2$), and niobium oxides (for example $Nb_2O_5$). It should generally be understood that when both the amine catalyst and the acid are supported, the solid supports of the amine catalyst and the acid may be the same or different.

For example, in one variation, both the amine catalyst and the acid include silica-alumina.

In other variations, the supported acid is a solid support that has been modified to include an acid moiety. Examples of acid moieties that may be present on such supports include a sulfonic acid moiety, a phosphoric acid moiety, and a carboxylic acid moiety. For example, a support may be modified such that 4-ethylbenzenesulfonic acid is attached to the support. In one variation, the amine catalyst is supported on silica-alumina, and additional silica-alumina is added without an amine moiety, which has been modified to contain a phosphoric acid moiety.

Suitable unsupported acids include acetic acid, benzoic acid, terephthalic acid, phthalic acid, isophthalic acid, adipic acid, succinic acid, oxalic acid, pimelic acid, valeric acid, muconic acid, mucic acid, toluic acid, citric acid, hydrochloric acid, nitric acid, sulfuric acid, boric acid, and phosphoric acid, or any combinations thereof. Any combinations of the acids described herein may be used. In one variation, the additional acid is acetic acid. In another variation, the additional acid is benzoic acid. In yet another variation, both acetic acid and benzoic acid are added as two additional acids.

Condensation Reaction

The amine catalyst described herein can catalyze the dimerization and/or trimerization of methyl ketones to produce α,β-unsaturated ketone(s). In some variations, the methyl ketone described herein may dimerize to produce an acyclic α,β-unsaturated ketone dimer product. In other variations, the methyl ketone may trimerize to produce a cyclic α,β-unsaturated ketone trimer product. In yet other variations, a mixture of cyclic trimer product and acyclic dimer product is produced.

It should generally be understood that the methyl ketones and α,β-unsaturated ketones discussed herein may include stereoisomers of those compounds.

For example, the ketones

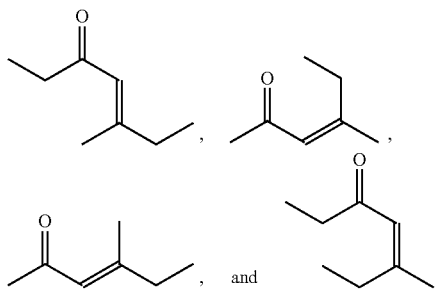

are stereoisomers.

The ketones

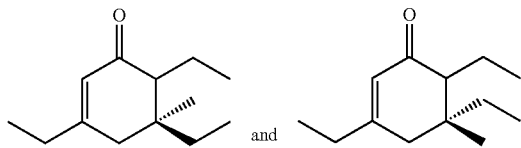

are also stereoisomers.

Methyl Ketone

The amine catalyst described herein can catalyze the condensation of a methyl ketone to produce an α,β-unsaturated ketone. While FIG. 1 depicts the use of methyl ketone 102, other methyl ketones may be used. The methyl ketone used to produce the α,β-unsaturated ketone may have the structure of Formula (A):

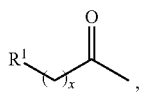
(A)

wherein:

$R^1$ is H, alkyl, carbocyclyl, or heterocyclyl;

x is an integer greater than or equal to 1.

In some variations, the alkyl, carbocyclyl, or heterocyclyl is unsubstituted or substituted with one or more substituents selected from hydroxyl, nitro, and halo.

In some embodiments of the methyl ketone having the structure of Formula (A), $R^1$ is alkyl. In certain embodiments, $R^1$ is unsubstituted alkyl. For example, $R^1$ may be methyl, ethyl, propyl, butyl, pentyl, hexyl, heptyl, octyl, nonyl, decyl, undecyl, or dodecyl. In certain embodiments, $R^1$ is alkyl substituted with one or more substituents selected from hydroxyl, nitro, chloro, bromo, and iodo.

In certain embodiments of the ketone having the structure of Formula (A), when $R^1$ is alkyl, the alkyl may be unbranched or branched. In some embodiments, the alkyl is branched. In certain embodiments, $R^1$ is isopropyl, isobutyl, tert-butyl, isopentyl, or tert-pentyl.

It should be understood that when $R^1$ is H and x is 1, the methyl ketone having the structure of Formula (A) is acetone. In some embodiments, when $R^1$ is H, x is an integer greater than 1, and the methyl ketone having the structure of Formula (A) is a methyl ketone other than acetone. In other embodiments, when $R^1$ is other than H, x is an integer greater than or equal to 1, and the methyl ketone having the structure of Formula (A) is a methyl ketone other than acetone.

In certain embodiments, x is an integer between 1 and 50, 1 and 40, 1 and 30, 2 and 30, or 3 and 30.

In certain embodiments of the methyl ketone having the structure of Formula (A), $R^1$ is carbocyclyl, or heterocyclyl.

Examples of methyl ketones that may be used in the methods described herein include:

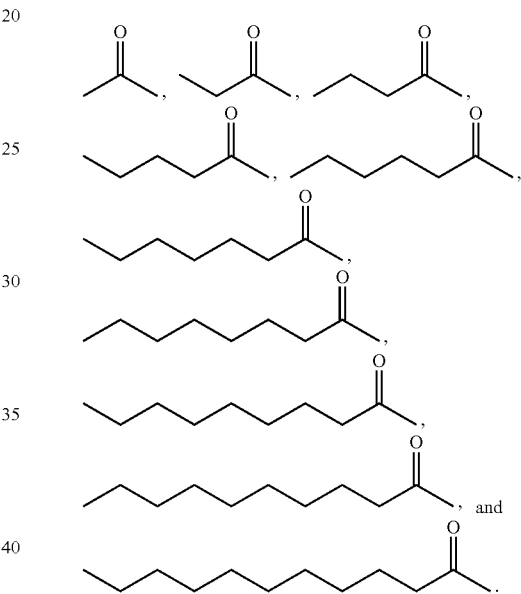

It should be understood that, in some embodiments, one methyl ketone having a structure of Formula (A), as described above may be used. Such ketone can undergo self-condensation to produce the α,β-unsaturated ketones described herein. In other embodiments, however, a mixture of methyl ketones independently having the structure of Formula (A) may be used. Such mixture of ketones can undergo different reactions to produce a mixture of different products. Self-condensation between methyl ketones having the same structure may produce α,β-unsaturated ketone dimer and trimer products, and cross-condensations between methyl ketones having different structures may produce a mixture of α,β-unsaturated ketones. In some embodiments, the α,β-unsaturated ketones produced will be only from self-condensation, while in other embodiments the α,β-unsaturated ketones produced will be only from cross-condensation. In other embodiments, the α,β-unsaturated ketones produced will be from both self-condensation and cross-condensation. Thus, provided herein is also a method for producing an α,β-unsaturated ketone or a mixture of α,β-unsaturated ketones, by contacting two or more methyl ketones independently having a structure of Formula (A) with an amine catalyst to produce at least one α,β-unsaturated ketone from at least a portion of the mixture of methyl ketones independently having the structure of Formula (A).

Fermentation Product Mixtures

The methyl ketone(s) provided for use in the methods described herein may be obtained from any commercially available sources, or accordingly to any methods generally known by one of skill in the art. In some embodiments, the methyl ketone(s) is/are produced from biological processes, such as by fermentation. For example, a fermentation product mixture may include acetone, which may be used as the methyl ketone starting material in the reaction to produce α,β-unsaturated ketones. With reference to FIG. 1, in some variations the methyl ketone 102 is provided in a fermentation product mixture.

The fermentation product mixture described herein may be derived from renewable sources, such as biomass. In some embodiments, the biomass is first converted into sugars, which is then used as the feedstock to produce the fermentation product mixture. In other embodiments, a mixture including sugars derived from biomass may be used as the feedstock to produce the fermentation product mixture. Sugars suitable for use as feedstock to produce the fermentation product mixture may include, for example, monosaccharides, disaccharides, or oligosaccharides. In certain embodiments, the sugars may include any $C_5$ saccharides or $C_6$ saccharides, or a combination of $C_5$ and $C_6$ saccharides. In other embodiments, the sugars may include arabinose, lyxose, ribose, xylose, ribulose, xylulose, allose, altrose, glucose, sucrose, cellobiose, mannose, gulose, idose, galactose, talose, psicose, fructose, sorbose, tagatose, xylobiose, glucose oligomers, xylose oligomers, or a mixture thereof. In one embodiment, the sugars may include glucose, sucrose or xylose, or a mixture thereof. In another embodiment, the sugars may include glucose or sucrose, or a mixture thereof. Any methods known in the art may be employed to produce sugars from the biomass. For example, the biomass may undergo pretreatment processes known in the art to more effectively liberate sugars from the biomass. The biomass is typically made up of organic compounds that are relatively high in oxygen, such as carbohydrates, and may also contain a wide variety of other organic compounds. In some embodiments, the biomass is made up of cellulose, hemicellulose, and/or lignin. Other suitable carbon sources for fermentation may include, for example, pectin, whey, butyric and acetic acids.

It should be understood, however, that in other embodiments, the sugars used as feedstock in the fermentation process may be derived from non-renewable sources, or from both renewable and non-renewable sources.

The fermentation product mixture may be produced by fermenting sugars using any host capable of producing methyl ketones. For example in some embodiments, the fermentation host is bacteria from the Clostridia family (e.g., *Clostridium acetobutylicum, Clostridium beijerinckii*). It should be understood, however, that any fermentation host capable of converting sugars into a mixture including a methyl ketone may be employed to provide the starting materials for the process described herein. For example, in some embodiments, the fermentation host is fungi.

In some embodiments, the fermentation product mixture may be used without further purification or isolation steps after the fermentation process. In other embodiments, the fermentation product mixture is isolated after the fermentation process. Any techniques known in the art may be used to isolate the fermentation product mixture after the fermentation process. Thus, provided herein is also a method of contacting a composition comprising biomass and/or sugars with a fermentation host to produce a fermentation product mixture, wherein the fermentation product mixture includes a methyl ketone, and contacting the fermentation product mixture with an amine catalyst as described herein to produce an α,β-unsaturated ketone from the condensation of the methyl ketone. In some embodiments, the fermentation host is selected from fungi and bacteria.

Additional methyl ketones may be added to the fermentation product mixture to vary the range of molecular weights and structures obtained from the process described herein. In some embodiments, these additional methyl ketones may be added to the fermentation product mixture before use in the reaction with the catalyst. In other embodiments, these additional methyl ketones may be added during the reaction. These additions to the fermentation product mixture may be useful for improving the product properties for specific applications, such as biodiesel. The methyl ketones added to the fermentation product mixture may be saturated or unsaturated.

The fermentation product mixture may also include bio-derived methyl ketones through ketonization of volatile fatty acids. For example, acetic acid may be ketonized via fermentation to form acetone, which can be converted into a mix of higher ketones using the methods described herein to produce gasoline and gasoline precursors.

Dimerization of Methyl Ketones

While FIG. 1 depicts the process to produce dimer product 110 from condensation of methyl ketone 102, in other variations other dimer products may be produced from the dimerization of other methyl ketones. The amine catalyst described herein can catalyze the dimerization of methyl ketones to produce α,β-unsaturated ketones of Formula (L), and any stereoisomers thereof, where Formula (L) is:

wherein $R^1$ and x are as defined for Formula (A) above.

It should be understood that the ketone of Formula (L) is the dimerization product of a methyl ketone of Formula (A), where a new C—C bond is formed between one methyl ketone and the alpha carbon of another methyl ketone, wherein the alpha carbon is the carbon immediately adjacent to the carbonyl carbon. For example, when $R^1$ is H and x is 1, the ketone of Formula (A) is

and the ketone of Formula (L) is

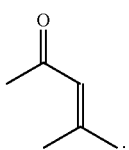

In another variation, when $R^1$ is methyl and x is 1, the ketone of Formula (A) is

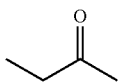

and the ketone of Formula (L) is

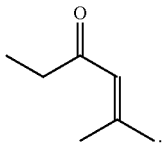

Trimerization of Methyl Ketones

While FIG. 1 depicts the process to produce dimer product 110 from condensation of methyl ketone 102, in other variations trimer products may be produced from the condensation of methyl ketones. The amine catalyst described herein can catalyze the trimerization of methyl ketones to produce α,β-unsaturated ketones of Formula (I), (II), (III), or (IV), or any stereoisomers thereof, or any combinations of the foregoing, wherein:

the ketone of Formula (I) is:

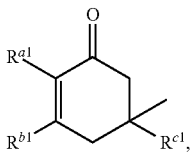

(I)

or any stereoisomers thereof, wherein:
$R^{a1}$ is —$(CH_2)_{x-1}R^1$;
$R^{b1}$ is —$(CH_2)_xR^1$; and
$R^{c1}$ is —$(CH_2)_xR^1$;
the ketone of Formula (II) is:

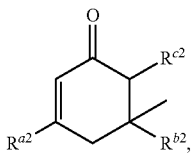

(II)

or any stereoisomers thereof, wherein:
$R^{a2}$ is —$(CH_2)_xR^1$;
$R^{b2}$ is —$(CH_2)_xR^1$; and
$R^{c2}$ is —$(CH_2)_{x-1}R^1$;
the ketone of Formula (III) is:

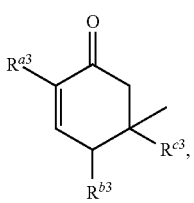

(III)

or any stereoisomers thereof, wherein:
$R^{a3}$ is —$(CH_2)_{x-1}R^1$;
$R^{b3}$ is —$(CH_2)_{x-1}R^1$; and
$R^{c3}$ is —$(CH_2)_xR^1$; and
the ketone of Formula (IV) is:

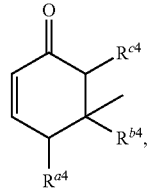

(IV)

or any stereoisomers thereof, wherein:
$R^{a4}$ is —$(CH_2)_{x-1}R^1$;
$R^{b4}$ is —$(CH_2)_xR^1$; and
$R^{c4}$ is —$(CH_2)_{x-1}R^1$;
wherein $R^1$ and x of Formulae (L), (I), (II), (III) and (IV) are as defined for Formula (A).

In some embodiments, the trimerization of a methyl ketone of Formula (A) produces a ketone of Formula (I), a ketone of Formula (II), a ketone of Formula (III), or ketone of Formula (IV). In other embodiments, the trimerization of a methyl ketone of Formula (A) produces ketones of Formula (I) and Formula (II), ketones of Formula (I) and Formula (III), ketones of Formula (I) and Formula (IV), ketones of Formula (II) and Formula (III), ketones of Formula (II) and Formula (IV), or ketones of Formula (III) and Formula (IV). In one embodiment, the trimerization of a methyl ketone of Formula (A) produces a mixture ketones of Formula (I), Formula (II), Formula (III), and Formula (IV).

It should be understood that contacting a methyl ketone of Formula (A) with the amine catalyst can produce dimer product, trimer product, or a mixture of dimer and trimer product. While FIG. 1 depicts the production of dimer product 110, in some variations a mixture of dimer and trimer product is produced. For example, if the methyl ketone of Formula (A) is

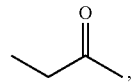

contacting the methyl ketone with an amine catalyst as described herein can produce

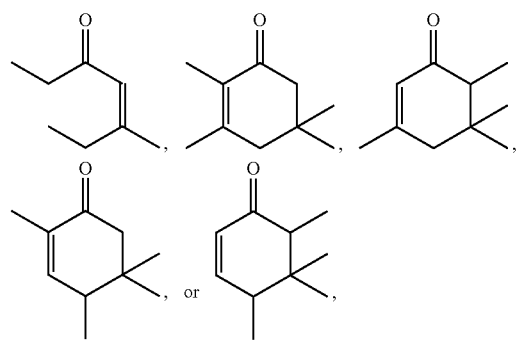

or any stereoisomers thereof, or any combination of the foregoing.

In some embodiments, at least 10%, at least 20%, at least 30%, at least 40%, at least 50%, at least 60%, at least 70%, at least 80%, or at least 90% of the product from contacting a methyl ketone of Formula (A) with the amine catalyst is a dimer product. In other embodiments, at least 40%, at least 50%, at least 60%, at least 70%, at least 80%, or at least 90% of the product from contacting a methyl ketone of Formula (A) with the amine catalyst is a dimer product. In yet other embodiments, at least 70%, at least 80%, or at least 90% of the product from contacting a methyl ketone of Formula (A) with the amine catalyst is a dimer product.

In some embodiments, reaction conditions may be chosen such that at least 50% of the product is a trimer product. For example, the reaction may be performed at a temperature chosen such that at least 50% of the product is a trimer product.

Various factors may cause the reaction to favor dimerization over trimerization. These factors may be chosen to tune the ratio of dimer to trimer products. Factors that allow the tuning of the reaction may include, for example, the temperature of the reaction or the ratio of reactant to catalyst. In one variation, performing the reaction at 473 K may produce both dimer and trimer product, while performing the reaction at 423 K may only produce dimer product. In another variation, performing the reaction with a 2 mmol of reactant and 100 mg of catalyst may only product dimer product, while performing the reaction with 2 mmol of reactant and 200 mg of catalyst may produce both dimer and trimer product.

In some embodiments, at least 10%, at least 20%, at least 30%, at least 40%, at least 50%, at least 60%, at least 70%, at least 80%, or at least 90% of the product from contacting a methyl ketone of Formula (A) with the amine catalyst is a trimer product. In other embodiments, at least 40%, at least 50% at least 60%, at least 70%, at least 80%, or at least 90% of the product from contacting a methyl ketone of Formula (A) with the amine catalyst is a trimer product. In yet other embodiments, at least 70%, at least 80%, or at least 90% of the product from contacting a methyl ketone of Formula (A) with the amine catalyst is a trimer product.

Provided herein is also an α,β-unsaturated ketone produced by any of the methods described herein. For example, provided herein is an α,β-unsaturated ketone produced by the method of contacting a methyl ketone with an amine catalyst. In another embodiment, provided herein is an α,β-unsaturated ketone produced by contacting a methyl ketone with an amine catalyst in the presence of an additional acid. In another embodiment, provided herein is an α,β-unsaturated ketone produced by contacting a methyl ketone of Formula (A) with a supported amine catalyst. The α,β-unsaturated ketone provided herein may be an α,β-unsaturated ketone of Formula (L), (I), (II), (III), or (IV), or any isomers thereof, or any combinations of the forgoing, produced by any of the methods described herein.

Provided herein is also a composition, comprising a methyl ketone, an amine catalyst, and an α,β-unsaturated ketone produced by any of the methods described herein. For example, provided herein is a composition, comprising a methyl ketone, an amine catalyst, and an α,β-unsaturated ketone produced by the method of contacting a methyl ketone with an amine catalyst. In another embodiment, provided herein is a composition, comprising a methyl ketone, an amine catalyst, and an α,β-unsaturated ketone produced by contacting a methyl ketone with an amine catalyst in the presence of an additional acid. In another embodiment, provided herein is a composition, comprising a methyl ketone of Formula (A), an amine catalyst, and an α,β-unsaturated ketone produced by contacting a methyl ketone of Formula (A) with an amine catalyst. The α,β-unsaturated ketone may be an α,β-unsaturated ketone of Formula (L), (I), (II), (III), or (IV), or any isomers thereof, or any combinations of the forgoing, produced by any of the methods described herein.

Separation and Recycling

The amine catalysts used in the methods described herein may be recycled. In some embodiments, the methods described herein further include separating the amine catalyst from the reaction mixture and/or recycling the amine catalyst. In some embodiments, the amine catalyst is separated from the product mixture, and then contacted by an additional reactant mixture. With reference again to FIG. 1, it should be generally understood that one or more steps may be omitted or added to process 100. For example, in some embodiments, amine catalyst 104 is isolated from the reaction mixture, and then contacted with additional methyl ketone.

Any methods known in the art may be used to separate the amine catalyst. For example, in one embodiment, a supported amine catalyst is separated from the product mixture by centrifugation. In another embodiment, an unsupported amine catalyst is separated from the product mixture by distillation. Separation of the amine catalyst may include multiple steps. For example, in one embodiment, a supported amine catalyst is separated from the product mixture by centrifugation, then washed with a solvent, and dried.

In other embodiments, the amine catalyst is contacted by additional reactants without separation from the product mixture. For example, additional fermentation product mixture may be added to the reaction vessel to further increase the overall product yield.

Recycling of the amine catalyst may also include recycling of one or more additional acids. For example, if the amine catalyst is supported on an acidic support, recycling of the amine catalyst could include recycling the acidic support.

Recycling of the amine catalyst may include the addition of one or more new acids. For example, in one embodiment, an unsupported amine catalyst is separated from a product mixture and a supported acid by distillation, and the separated amine catalyst is combined with a second reactant mixture and a second supported acid to catalyze a second reaction.

The Solvent

In some embodiments, the methods of producing the ketones using an amine catalyst described herein are performed neat, i.e., without addition of a solvent. However, in other embodiments, the methods of producing the ketones using an amine catalyst may be performed with a solvent. With reference to FIG. 1, while the use of amine catalyst 104 is depicted in the absence of solvent, in some variations a solvent may be additionally included in the reaction mixture.

Any solvent that promotes condensation of the methyl ketones may be employed in the process described herein. For example, the solvent may be an organic solvent. Organic solvents may include aromatics (e.g., toluene, benzene), acetates (e.g., ethyl acetate or isopropylacetate), nitriles (e.g., acetonitrile), or ethers (e.g., diglyme, monoglyme, diglybu, THF). As used herein, "diglyme" refers to diethylene glycol dimethyl ether. As used herein, "diglybu" refers to diethylene glycol dibutyl ether. In some embodiments, the solvent may include toluene, xylenes, dimethylsulfoxide, dimethylformamide, tetrahydrofuran, or $C_6$-$C_{12}$ alkanes. In one embodiment, the solvent includes toluene.

The Reaction Conditions

Reaction Phase

The methyl ketones, amine catalysts, and acids in the methods described herein can be provided in any phase, or mixture of phases, that promotes the condensation of the methyl ketones to produce α,β-unsaturated ketones. The α,β-unsaturated ketones produced may be in any phase. These phases include the gas phase, liquid phase, solid phase, or any combination thereof.

In one embodiment, condensation of a methyl ketone occurs with a gas phase methyl ketone and solid phase supported amine catalyst to produce a gas phase ketone. In another embodiment, condensation of a methyl ketone occurs with a liquid phase methyl ketone and solid phase supported amine catalyst to produce a liquid phase ketone. In another embodiment, condensation of a methyl ketone occurs with a liquid phase methyl ketone, liquid phase amine catalyst, and liquid phase acid to produce a liquid phase ketone.

Operating Temperature

The methods described herein may be performed at any suitable temperature to produce the ketones.

The operating temperature range selected may vary depending on various factors, including the solvent, amine catalyst, acid, and metal catalyst if used. In some embodiments, the operating temperature range is between about 350 K to about 550 K, between about 350 K to about 500 K, or between about 400 K to about 450 K.

In some embodiments, the reaction may be exothermic and inter-stage cooling may be utilized to maintain the temperature at the operating temperature.

Operating Pressure

The operating pressure of the methods described herein to produce the ketones may vary. The operating pressure refers to the pressure across a reaction zone. In some embodiments, the operating pressure in between 1 atm and 60 atm.

Reaction Time

In some embodiments, the reaction may be carried out for 24 hours, but the time of the reaction will also vary with the reaction conditions (e.g., reaction temperature), catalyst activity, desired yield, and desired conversion (e.g., low conversion with recycle). In some embodiments, the reaction time is determined by the rate of conversion of the starting material. In some embodiments, the reaction mixture is heated for 10 minutes to 30 hours. In other embodiments, the reaction mixture is heated for 10 to 24 hours. In yet other embodiments, the reaction mixture is heated for 18 to 24 hours. In yet other embodiments, the reaction is heated for 1 to 10 hours. In yet other embodiments, the reaction mixture is heated for 10 minutes to 10 hours.

Other Process Considerations

In some embodiments, the reaction is in a batch reactor. In other embodiments, the reaction would is in a flow reactor. In yet other embodiments, the reaction is in a plug flow reactor (PFR), such as a packed bed reactor, as either a single reactor or a multiple tube reactor. In some embodiments, unreacted feedstocks and/or one or more intermediate reaction products are separated from the products downstream of the reactor and recycled back into the reaction zone to be contacted with the amine catalyst.

Provided is a ketone obtained by any of the methods set forth herein. Thus, in one embodiment, provided herein is an α,β-unsaturated ketone obtained by contacting a methyl ketone with an amine catalyst. In another embodiment, provided herein is an α,β-unsaturated ketone obtained by contacting a methyl ketone with an amine catalyst in the presence of an additional acid. In one variation, provided herein is an α,β-unsaturated ketone obtained by contacting a methyl ketone with a secondary amine moiety supported on silica alumina. In one variation, provided herein is an α,β-unsaturated ketone produced by contacting butan-2-one with a N-(2-aminoethyl)3-aminopropyl moiety supported on silica-alumina. In another variation, provided herein is an α,β-unsaturated ketone obtained by contacting heptan-2-one with diethylamine in the presence of acetic acid. In another embodiment, the ketone may be produced by contacting heptan-2-one with piperidine in the presence of acetic acid.

Uses of the Ketone Products

The α,β-unsaturated ketones produced by any of the methods described herein may be suitable for use as fuels, gasoline additives, and/or lubricants, and precursors thereof. For example, in some variations, the α,β-unsaturated ketones containing 5 to 24 carbon atoms are suitable for use in producing fuels. In other variations, the α,β-unsaturated ketones containing at least 24 carbon atoms are suitable for use in producing lubricants. In yet other variations, the α,β-unsaturated ketones containing 5 to 24 carbon atoms are suitable for use in producing gasoline additives.

Such ketones may be hydrodeoxygenated to produce their corresponding alkanes. For example, the cyclic and acyclic ketones can be hydrodeoxygenated to produce alkanes. Such alkanes may be used as fuels, gasoline additives, or lubricants. One of skill in the art would recognize the suitable catalyst and reactions conditions that may be used to perform the hydrodeoxygenation reaction. For example, the hydrodeoxygenation catalyst may include Ni, Pt, Pd, Rh, Ru, Cu, and other transition metals. In combination with metals, acidic supports such $NbOPO_4$, $Nb_2O_3$, $SiO_2$—$Al_2O_3$, $Ta_2O_5$, $TiO_2$, $ZrO_2$, and sulfated $ZrO_2$ may also be used to provide hydrogenation activity. One such catalyst is Pt/$NbOPO_4$. Thus, in some aspects, provided herein are methods to convert the α,β-unsaturated ketones into alkanes for use as fuels or lubricants.

The α,β-unsaturated ketone(s) produced by the methods described herein may also be reduced (e.g., hydrogenated) to produce their corresponding alcohols. Such alcohols may be used as fuels, gasoline additives, and/or lubricants, or precursors thereof. One of skill in the art would recognize the suitable catalyst and reactions conditions that may be used to perform the reduction reaction. For example, the catalysts described above for hydrodeoxygenation to produce alkanes may also be used to produce alcohols, for example, under milder reaction conditions. Thus, in some aspects, provided herein are methods to convert the α,β-unsaturated ketones into alcohols for use as fuels, gasoline additives, and/or lubricants, or precursors thereof.

The hydrodeoxygenation and/or hydrogenating of ketone(s) produced by the methods described herein may also produce a mixture of alkanes and alcohols, suitable for use as fuels, fuel additives, and/or lubricants, or precursors thereof.

Compositions

Provided are also compositions including any of the amine catalysts as described herein, and any of the methyl ketones as described herein. The composition may additionally include an acid, which may include any of the acids described herein.

In one variation, provided herein is a composition that includes: a methyl ketone and an amine catalyst. In another variation, provided herein is a composition, comprising a methyl ketone, an amine catalyst, and an α,β-unsaturated ketone obtained by contacting the methyl ketone with the amine catalyst. In yet another variation, provided herein is a composition, comprising a methyl ketone, an amine catalyst, and an additional acid. In another embodiment, provided herein is a composition, comprising a methyl ketone, an amine catalyst, an additional acid, and α,β-unsaturated ketone obtained by contacting the methyl ketone with the amine catalyst.

In some embodiments, the amine catalyst is supported. In other embodiments, the amine catalyst is unsupported. For example, in one embodiment, when the amine catalyst includes a secondary amine moiety supported on silica-alumina, the composition includes butan-2-one and a secondary amine moiety supported on silica-alumina. In one embodiment, the composition includes butan-2-one and a N-(2-aminoethyl)3-aminopropyl moiety supported on silica-alumina.

In some embodiments, the acid is a supported acid. In other embodiments, the acid is an unsupported acid. For example, in one variation, the composition includes heptan-2-one, diethylamine, and acetic acid. In another variation, the composition includes heptan-2-one, proline, and acetic acid.

In yet other embodiments, the composition includes a solvent. For example, in one variation, provided herein is a composition, comprising a methyl ketone, an amine catalyst, and an optional solvent.

In any of the foregoing embodiments of the composition, the composition further includes water.

As used herein, "alkyl" refers to a linear or branched saturated hydrocarbon chain. Examples of alkyl groups include methyl, ethyl, n-propyl, iso-propyl, n-butyl, sec-butyl, tert-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl. In some embodiments, alkyl as used herein, such as in compounds of Formula (A), (L), (I), (II), (III), and (IV), has 1 to 30 carbon atoms (i.e., $C_{1-30}$ alkyl), 1 to 20 carbon atoms (i.e., $C_{1-20}$ alkyl), 1 to 15 carbon atoms (i.e., $C_{1-15}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), or 1 carbon atom (i.e., $C_1$ alkyl).

As used herein, "heterocycle" refers to a cyclic compound with one or more ring heteroatoms. In some variations, the heteroatoms are independently selected from nitrogen, oxygen, sulfur, and phosphorous. Heterocycles can include one or more rings, include fused and bridged groups, and can be saturated or have any degree of unsaturation. Examples of heterocycles include, for example, pyrrolidine, piperidine, piperazine, oxetane, dioxolane, azetidine, morpholine, furan, pyrrol, thiophenyl, imidazole, thiazole, pyridazine, pyrimidine, and pyrazole. In some embodiments, heterocycle as used herein, such as in compounds of Formula (A), has 2 to 40 ring carbon atoms (i.e., $C_{2-40}$ heterocycle), 2 to 30 ring carbon atoms (i.e., $C_{2-30}$ heterocycle), 2 to 20 ring carbon atoms (i.e., $C_{2-20}$ heterocycle), 2 to 15 ring carbon atoms (i.e., $C_{2-15}$ heterocycle), 2 to 12 ring carbon atoms (i.e., $C_{2-12}$ heterocycle), 2 to 10 ring carbon atoms (i.e., $C_{2-10}$ heterocycle), or 2 to 8 ring carbon atoms (i.e., $C_{2-8}$ heterocycle); and 1 to 8 ring heteroatoms, 1 to 6 ring heteroatoms, 1 to 4 ring heteroatoms, 1 to 3 ring heteroatoms, 1 or 2 ring heteroatoms, or 1 ring heteroatom independently selected from nitrogen, sulfur, oxygen, or phosphorous. "Heterocyclyl" refers to the radical moiety of the equivalent heterocycle. An example of a heterocyclyl is piperidinyl, corresponding to the radical moiety of the heterocycle piperidine.

As used herein, "carbocycle" refers to a cyclic compound in which all the ring atoms are carbon atoms. Carbocycles can include one or more rings, including fused and bridged groups, and can be saturated or have any degree of unsaturation. Carbocycles may include, for example, cycloalkyl compounds and aryl compounds. Examples of carbocycles include, for example, benzene, naphthalene, anthracine, cyclopropane, cyclobutane, cyclopentane, cyclohexane, cyclopentene, and cyclohexene. In some embodiments, carbocycle as used herein, such as in compounds of Formula (A), has 2 to 40 ring carbon atoms (i.e., $C_{2-40}$ carbocycle), 2 to 30 ring carbon atoms (i.e., $C_{2-30}$ carbocycle), 2 to 20 ring carbon atoms (i.e., $C_{2-20}$ carbocycle), 2 to 15 ring carbon atoms (i.e., $C_{2-15}$ carbocycle), 2 to 12 ring carbon atoms (i.e., $C_{2-12}$ carbocycle), 2 to 10 ring carbon atoms (i.e., $C_{2-10}$ carbocycle), or 2 to 8 ring carbon atoms (i.e., $C_{2-8}$ carbocycle). "Carbocyclyl" refers to the radical moiety of the equivalent carbocycle. An example of a carbocyclyl is cyclohexyl, corresponding to the radical moiety of the carbocycle cyclohexane.

As used herein, "ether" refers to —R—O—R', wherein R and R' are independently alkyl, carbocycle, or hetereocycle. Examples of ethers include dimethyl ether, diethyl ether, methyl ethyl ether, and methyl tert-butyl ether. A substituted ether may be formed by replacing one or more hydrogen atoms on the R or R' with a moiety other than hydrogen, provided that the designated atom's normal valence is not exceeded.

As used herein, "thioether" refers to —R—S—R', wherein R and R' are independently alkyl, carbocycle, or hetereocycle. Examples of thioethers include dimethyl thioether, diethyl thioether, methyl ethyl thioether, and methyl tert-butyl thioether. A substituted thioether may be formed by replacing one or more hydrogen atoms on the R or R' with a moiety other than hydrogen, provided that the designated atom's normal valence is not exceeded.

The term "substituted", as used herein, means that any one or more hydrogen atoms on the designated atom or group is replaced with a moiety other than hydrogen, provided that the designated atom's normal valence is not exceeded.

It should be understood that when a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

It should be understood that reference to "between" two values or parameters herein includes (and describes) embodiments that include those two values or parameters per se. For example, description referring to "between x and y" includes description of "x" and "y" per se.

Enumerated Embodiments

The following enumerated embodiments are representative of some aspects of the invention.
1. A method of producing an α,β-unsaturated ketone, comprising:
   contacting a methyl ketone of Formula (A) with an amine catalyst; and producing an α,β-unsaturated ketone from at least a portion of the methyl ketone by a condensation reaction, wherein:

the methyl ketone of Formula (A) is:

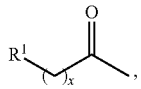
(A)

wherein:
R¹ is H, alkyl, carbocyclyl, or heterocyclyl;
wherein the alkyl, carbocyclyl, or heterocyclyl is unsubstituted or substituted with one or more substituents independently selected from the group consisting of hydroxyl, nitro, and halo; and
x is an integer greater than or equal to 1.

2. The method of embodiment 1, wherein the α,β-unsaturated ketone is a compound of Formula (L):

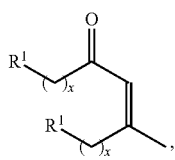
(L)

or any isomers thereof, wherein R¹ and x are as defined for Formula (A).

3. The method of embodiment 1 or 2, wherein the contacting of the methyl ketone of Formula (A) with the amine catalyst forms an enamine complex.

4. The method of embodiment 2 or 3, wherein:
water is present at a concentration of at least 0.6 gram water per gram amine catalyst; and
the % yield of the α,β-unsaturated ketone of Formula (L) produced decreases less than 20% over 16 hours.

5. The method of any one of embodiments 2 to 4, wherein the α,β-unsaturated ketone of Formula (L), or any isomers thereof, is produced with a yield of at least 10% at a weight hourly space velocity of about 0.2 grams of ketone of Formula (A) per gram of catalyst per hour.

6. The method of any one of embodiments 1 to 5, further comprising contacting a composition comprising biomass or sugars with a fermentation host to produce a fermentation product mixture, wherein the fermentation product mixture comprises the methyl ketone of Formula (A).

7. The method of embodiment 6, wherein the fermentation host is selected from the group consisting of bacteria and fungi.

8. The method of any one of embodiments 2 to 7, further comprising producing an α,β-unsaturated cyclic ketone of Formula (I), (II), (III), or (IV), or any isomers thereof, or any combinations of the foregoing, from at least a portion of the methyl ketone of Formula (A) by a condensation reaction, wherein:

the α,β-unsaturated cyclic ketone of Formula (I) is:

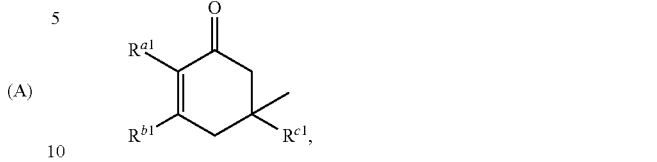
(I)

or any isomers thereof, wherein:
$R^{a1}$ is —$(CH_2)_{x-1}R^1$;
$R^{b1}$ is —$(CH_2)_xR^1$; and
$R^{c1}$ is —$(CH_2)_xR^1$;

the α,β-unsaturated cyclic ketone of Formula (II) is:

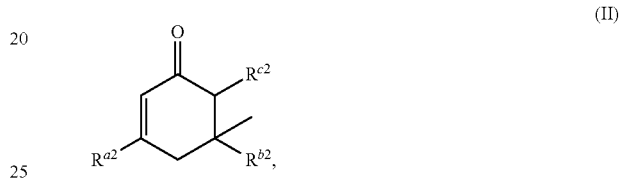
(II)

or any isomers thereof, wherein:
$R^{a2}$ is —$(CH_2)_xR^1$;
$R^{b2}$ is —$(CH_2)_xR^1$; and
$R^{c2}$ is —$(CH_2)_{x-1}R^1$;

the α,β-unsaturated cyclic ketone of Formula (III) is:

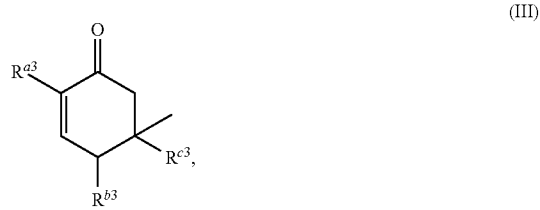
(III)

or any isomers thereof, wherein:
$R^{a1}$ is —$(CH_2)_{x-1}R^1$;
$R^{b3}$ is —$(CH_2)_{x-1}R^1$; and
$R^{c3}$ is —$(CH_2)_xR^1$;

the α,β-unsaturated cyclic ketone of Formula (IV) is:

(IV)

or any isomers thereof, wherein:
$R^{a4}$ is —$(CH_2)_{x-1}R^1$;
$R^{b4}$ is —$(CH_2)_xR^1$; and
$R^{c4}$ is —$(CH_2)_{x-1}R^1$;

wherein R¹ and x of Formula (L), (I), (II), (III) and (IV) are as defined for Formula (A).

9. The method of embodiment 8, wherein the α,β-unsaturated ketone of Formula (L), or any isomers thereof, and the α,β-unsaturated cyclic ketone of Formula (I), (II), (III) and/or (IV), or any isomers thereof form a product mixture, wherein the α,β-unsaturated ketone of Formula (L) comprises at least 70% of the product mixture.

10. The method of embodiment 9, wherein the α,β-unsaturated ketone of Formula (L) comprises at least 80% of the product mixture.

11. The method of embodiment 9, wherein the α,β-unsaturated ketone of Formula (L) comprises at least 90% of the product mixture.

12. The method of embodiment 9, wherein the α,β-unsaturated ketone of Formula (L) comprises between 70% and 99% of the product mixture.

13. The method of embodiment 9, wherein the α,β-unsaturated ketone of Formula (L) comprises between 80% and 99% of the product mixture.

14. The method of any one of embodiments 1 to 13, further comprising:
isolating the amine catalyst from the α,β-unsaturated ketone to obtain an isolated amine catalyst.

15. The method of embodiment 14, further comprising:
contacting an additional methyl ketone of Formula (A) with the isolated amine catalyst; and
producing an additional α,β-unsaturated ketone from at least a portion of the methyl ketone by a condensation reaction.

16. The method of any one of embodiments 1 to 15, wherein the amine catalyst comprises an amine moiety having the structure:

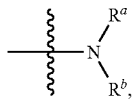

wherein $R^a$ and $R^b$ at each occurrence are independently H, alkyl, carbocyclyl, heterocyclyl, or ether, or any combinations thereof;
wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;
or $R^a$ and $R^b$ are taken together with the nitrogen atom to which they are both attached to form a heterocycle,
wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.

17. The method of embodiment 16, wherein $R^a$ and $R^b$ are taken together with the nitrogen atom to which they are both attached to form a heterocycle, wherein the heterocycle comprises:
1 to 8 heteroatoms;
wherein the heteroatoms are independently selected from the group consisting of N, O, S, and P;
1 to 30 carbon ring atoms; and
the heterocycle is unsubstituted or substituted with one or more substituents selected from the group consisting of alkyl, hydroxyl, amine, oxo, carboxyl, imine, carbocyclyl, heterocyclyl, halo, ether, and thioether.

18. The method of any one of embodiments 1 to 17, wherein the amine catalyst comprises an amine moiety, wherein the amine moiety comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

19. The method of embodiment 18, wherein the heterocycle comprises 1 to 30 carbon atoms and 1 to 8 heteroatoms, wherein the heteroatoms are independently selected from the group consisting of N, O, S, and P.

20. The method of any one of embodiments 1 to 19, wherein the amine catalyst further comprises a solid support and a linker, wherein the linker attaches the amine moiety to the solid support.

21. The method of embodiment 20, wherein the solid support comprises silica, alumina, silica-alumina, $TiO_2$, $ZrO_2$, or $Nb_2O_5$, or any combinations thereof.

22. The method of embodiment 20 or 21, wherein the solid support comprises silica-alumina.

23. The method of any one of embodiments 20 to 22, wherein the solid support is porous.

24. The method of any one of embodiments 20 to 23, wherein the solid support comprises a plurality of pores, wherein at least a portion of the pores have a pore diameter between 2 nm and 50 nm.

25. The method of embodiment 24, wherein the pore diameter is between 2 nm and 40 nm.

26. The method of embodiment 24 or 25, wherein the pore diameter is between 2 nm and 30 nm.

27. The method of any one of embodiments 20 to 26, wherein the solid support comprises a mesoporous silica selected from the group consisting of MCM-41, SBA-15, and KIT-6.

28. The method of any one of embodiments 20 to 27, wherein the solid support comprises an acid moiety.

29. The method of embodiment 28, wherein the acid moiety is selected from the group consisting of carboxylic, phosphoric, and sulfonic, or any combinations thereof.

30. The method of any one of embodiments 20 to 29, wherein the solid support comprises silicon, aluminum, germanium, boron, or phosphorous atoms, or any combinations thereof.

31. The method of any one of embodiments 20 to 30, wherein the solid support comprises a moiety having a structure of formula M-Y—Z, wherein:
M is silica, alumina, silica-alumina, $TiO_2$, $ZrO_2$, $Nb_2O_5$, or any combinations thereof;
Y is silicon, aluminum, germanium, boron, or phosphorous; and
Z is a linker connecting Y and the amine moiety.

32. The method of any one of embodiments 20 to 31, wherein the linker comprises:
-alkyl-, -aliphatic-, -aryl-, -carbocycle-, -heterocycle-, -sulfone-, substituted or unsubstituted -ether-, or any combinations thereof;
wherein the -alkyl-, -aliphatic-, -aryl-, -carbocycle-, -heterocycle-, -sulfone-, -ether- are unsubstituted or substituted with one or more substituents independently selected from the group consisting of alkyl, hydroxyl, amine, oxo, carboxyl, imine, carbocyclyl, and heterocyclyl.

33. The method of any one of embodiments 20 to 32, wherein the linker comprises at least three linear chain atoms.

34. The method of any one of embodiments 20 to 33, wherein the linker comprises 3 to 30 linear chain atoms.

35. The method of any one of embodiments 20 to 34, wherein the linker comprises 3 to 20 linear chain atoms.

36. The method of any one of embodiments 1 to 35, wherein the amine catalyst comprises a secondary amine.

37. The method of any one of embodiment 16 to 35, wherein the amine moiety is selected from the group consisting of:

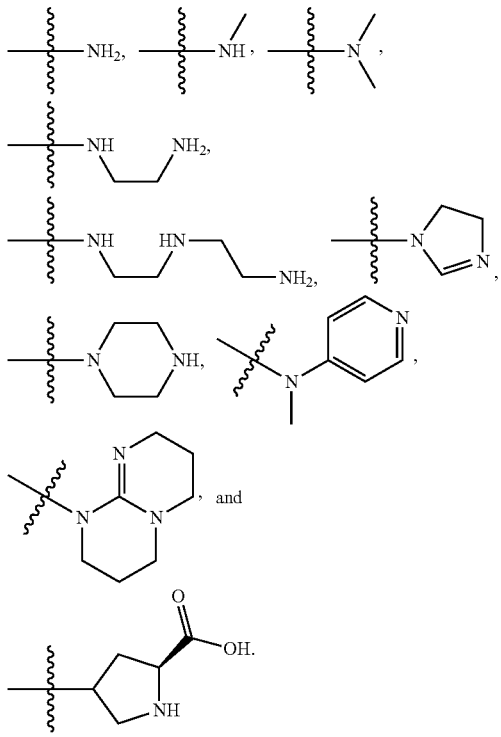

38. The method of any one of embodiments 1 to 35, or 37, wherein the amine catalyst comprises:

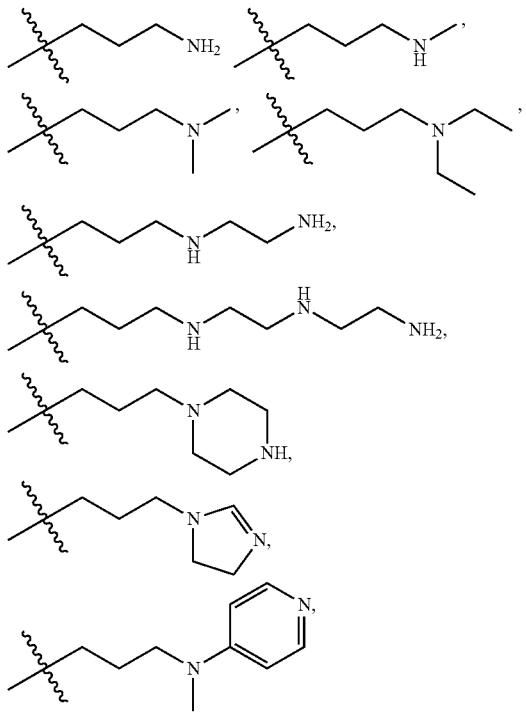

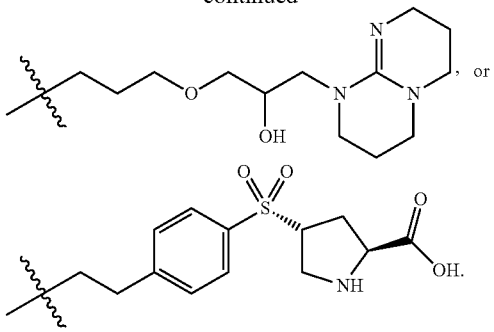

39. The method of any one of embodiments 20 to 38, wherein the linker comprises:

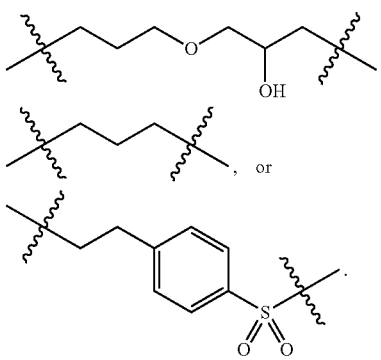

40. The method of any one of embodiments 1 to 39, wherein the methyl ketone is contacted with the amine catalyst in the presence of an acid.

41. The method of embodiment 40, wherein the amine catalyst is an unsupported amine catalyst.

42. The method of embodiment 40 or 41, wherein the amine catalyst is selected from the group consisting of diethylamine, piperazine, pyrrolidine, proline, imidazole, pyridine, triazabicyclodecene, and 4-dimethylaminopyridine.

43. The method of any one of embodiments 40 to 42, wherein the amine catalyst is selected from the group consisting of pyrrolidine, piperazine, and proline.

44. The method of any one of embodiments 40 to 43, wherein the acid is supported or unsupported.

45. The method of any one of embodiments 40 to 44, wherein the acid is supported on a support comprising silica, silica-alumina, alumina, $TiO_2$, $ZrO_2$, $Nb_2O_5$, or any combinations thereof.

46. The method of any one of embodiments 40 to 44, wherein the acid is selected from the group consisting of acetic acid, benzoic acid, terephthalic acid, phthalic acid, isophthalic acid, adipic acid, succinic acid, oxalic acid, pimelic acid, valeric acid, muconic acid, mucic acid, toluic acid, citric acid, and mineral acids, or any combinations thereof.

47. The method of any one of embodiments 40 to 46, wherein the acid comprises a carboxylic acid moiety.

48. The method of any one of embodiments 40 to 44, wherein the acid is selected from the group consisting of acetic acid and benzoic acid.

49. The method of any one of embodiments 1 to 48, wherein the methyl ketone of Formula (A) is provided in a fermentation product mixture.

50. The method of any one of embodiments 1 to 48, wherein the methyl ketone of Formula (A) and the amine catalyst are further contacted by a solvent.
51. The method of embodiment 50, wherein the solvent comprises toluene, xylenes, dimethyl sulfoxide, dimethylfuran, tetrahydrofuran, alkanes, or any combination thereof.
52. The method of embodiment 50 or 51, wherein the solvent comprises toluene.
53. The method of any one of embodiments 1 to 52, wherein the methyl ketone of Formula (A) is contacted with the amine catalyst at an operating temperature range from 350 to 550 K.
54. The method of any one of embodiments 1 to 53, wherein x is an integer from 1 to 30.
55. The method of any one of embodiments 1 to 54, wherein the methyl ketone of Formula (A) is selected from the group consisting of acetone, butan-2-one, pentan-2-one, hexan-2-one, heptan-2-one, octan-2-one, nonan-2-one, decan-2-one, undecan-2-one, dodecan-2-one, tridecan-2-one, tetradecan-2-one, pentadecan-2-one, hexadecane-2-one, heptadecan-2-one, octadecan-2-one, nonadecan-2-one, and icosan-2-one.
56. The method of any one of embodiments 1 to 55, wherein the methyl ketone of Formula (A) is selected from the group consisting of acetone, butan-2-one, pentan-2-one, hexan-2-one, heptan-2-one, octan-2-one, nonan-2-one, decan-2-one, undecan-2-one, dodecan-2-one, tridecan-2-one, tetradecan-2-one, pentadecan-2-one.
57. The method of any one of embodiments 1 to 56, wherein the methyl ketone of Formula (A) is selected from the group consisting of butan-2-one, pentan-2-one, hexan-2-one, heptan-2-one, octan-2-one, nonan-2-one, decan-2-one, undecan-2-one, dodecan-2-one, tridecan-2-one, tetradecan-2-one, pentadecan-2-one.
58. The method of any one of embodiments 1 to 54, or 57, wherein when $R^1$ is H, x is an integer greater than 1.
59. The method of any one of embodiments 1 to 54, or 57, wherein when x is 1, $R^1$ is other than H.
60. The method of any one of embodiments 1 to 54, or 57 to 59, wherein the methyl ketone of Formula (A) is other than acetone.
61. A method, comprising:
producing an α,β-unsaturated ketone according to the method of any one of embodiments 1 to 60; and
hydrodeoxygenating the α,β-unsaturated ketone to produce an alkane.
62. A method, comprising:
producing an α,β-unsaturated ketone according to the methods of any one of embodiments 1 to 60; and
reducing the α,β-unsaturated ketone to produce an alcohol.
63. An α,β-unsaturated ketone produced according to any one of the methods of embodiments 1 to 60.
64. An alkane produced according to the method of embodiment 61.
65. An alcohol produced according to the method of embodiment 62.
66. A composition, comprising:
a methyl ketone of Formula (A), and an amine catalyst, wherein:
the methyl ketone of Formula (A) is:

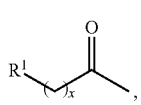

(A)

wherein:
$R^1$ is H, alkyl, carbocyclyl, or heterocyclyl;
wherein the alkyl, carbocyclyl, or heterocyclyl is unsubstituted or substituted with one or more substituents selected from the group consisting of hydroxyl, and halo; and
x is an integer greater than or equal to 1.
67. The composition of embodiment 66, further comprising an α,β-unsaturated ketone.
68. The composition of embodiment 67, wherein the α,β-unsaturated ketone is of Formula (L):

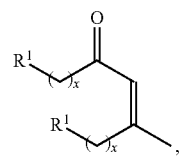

(L)

or any isomers thereof, wherein $R^1$ and x are as defined for Formula (A).
69. The composition of embodiment 67 or 68, further comprising an α,β-unsaturated ketone of Formula (I), (II), (III), or (IV), or any isomers thereof, or any combinations of the foregoing, wherein:
the ketone of Formula (I) is:

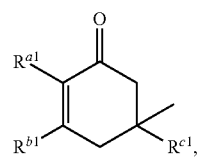

(I)

or any isomers thereof, wherein:
$R^{a1}$ is —$(CH_2)_{x-1}R^1$;
$R^{b1}$ is —$(CH_2)_xR^1$; and
$R^{c1}$ is —$(CH_2)_xR^1$;
the ketone of Formula (II) is:

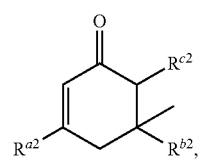

(II)

or any isomers thereof, wherein:
$R^{a2}$ is —$(CH_2)_xR^1$;
$R^{b2}$ is —$(CH_2)_xR^1$; and
$R^{c2}$ is —$(CH_2)_{x-1}R^1$;
the ketone of Formula (III) is:

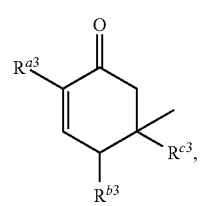

(III)

or any isomers thereof, wherein:
$R^{a3}$ is —$(CH_2)_{x-1}R^1$;
$R^{b3}$ is —$(CH_2)_{x-1}R^1$; and
$R^{c3}$ is —$(CH_2)_xR^1$;
the ketone of Formula (IV) is:

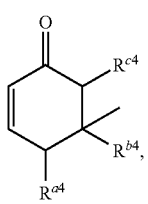

(IV)

or any isomers thereof, wherein:
$R^{a4}$ is —$(CH_2)_{x-1}R^1$;
$R^{b4}$ is —$(CH_2)_xR^1$; and
$R^{c4}$ is —$(CH_2)_{x-1}R^1$;
wherein $R^1$ and x of Formula (L), (I), (II), (III) and (IV) are as defined for Formula (A).

70. The composition of embodiment 69, wherein the α,β-unsaturated ketone of Formula (L), or any isomers thereof, and the α,β-unsaturated cyclic ketone of Formula (I), (II), (III) and/or (IV), or any isomers thereof form a product mixture, wherein the α,β-unsaturated ketone of Formula (L) comprises at least 70% of the product mixture.

71. The composition of embodiment 70, wherein the α,β-unsaturated ketone of Formula (L) comprises at least 70% of the α,β-unsaturated ketone.

72. The composition of embodiment 70, wherein the α,β-unsaturated ketone of Formula (L) comprises at least 80% of the of the α,β-unsaturated ketone.

73. The composition of embodiment 70, wherein the α,β-unsaturated ketone of Formula (L) comprises at least 90% of the α,β-unsaturated ketone.

74. The composition of embodiment 70, wherein the α,β-unsaturated ketone of Formula (L) comprises between 70% and 99% of the α,β-unsaturated ketone.

75. The composition of any one of embodiments 66 to 74, wherein x is an integer from 1 to 30.

76. The composition of any one of embodiments 66 to 75, wherein the methyl ketone of Formula (A) is selected from the group consisting of acetone, butan-2-one, pentan-2-one, hexan-2-one, heptan-2-one, octan-2-one, nonan-2-one, decan-2-one, undecan-2-one, dodecan-2-one, tridecan-2-one, tetradecan-2-one, pentadecan-2-one, hexadecane-2-one, heptadecan-2-one, octadecan-2-one, nonadecan-2-one, and icosan-2-one.

77. The composition of any one of embodiments 66 to 75, wherein the methyl ketone of Formula (A) is selected from the group consisting of acetone, butan-2-one, pentan-2-one, hexan-2-one, heptan-2-one, octan-2-one, nonan-2-one, decan-2-one, undecan-2-one, dodecan-2-one, tridecan-2-one, tetradecan-2-one, pentadecan-2-one.

78. The composition of any one of embodiments 66 to 75, wherein the methyl ketone of Formula (A) is selected from the group consisting of butan-2-one, pentan-2-one, hexan-2-one, heptan-2-one, octan-2-one, nonan-2-one, decan-2-one, undecan-2-one, dodecan-2-one, tridecan-2-one, tetradecan-2-one, pentadecan-2-one.

79. The composition of any one of embodiments 66 to 74, wherein when $R^1$ is H, x is an integer greater than 1.

80. The composition of any one of embodiments 66 to 74, wherein when x is 1, $R^1$ is not H.

81. The composition of any one of embodiments 66 to 74, wherein the methyl ketone of Formula (A) is not acetone.

82. The composition of any one of embodiments 66 to 81, wherein the amine catalyst comprises a solid support, an amine moiety, and a linker, wherein the linker attaches the amine moiety to the solid support.

83. The composition of embodiment 82, wherein the solid support comprises silica, alumina, silica-alumina, $TiO_2$, $ZrO_2$, $Nb_2O_5$, or any combinations thereof.

84. The composition of embodiment 82 or 83, wherein the solid support comprises silica-alumina.

85. The composition of any one of embodiments 82 to 84, wherein the solid support is porous.

86. The composition of any one of embodiments 82 to 85, wherein the solid support comprises a plurality of pores, wherein at least a portion of the pores have a pore diameter, and wherein the pore diameter is between 2 nm and 50 nm.

87. The composition of embodiment 86, wherein the pore diameter is between 2 nm and 40 nm.

88. The composition of embodiment 86, wherein the pore diameter is between 2 nm and 30 nm.

89. The composition of any one of embodiments 82 to 88, wherein the solid support comprises a mesoporous silica selected from the group consisting of MCM-41, SBA-15, and KIT-6.

90. The composition of any one of embodiments 82 to 89, wherein the solid support comprises an acid moiety.

91. The composition of embodiment 90, wherein the acid moiety is selected from the group consisting of carboxylic, phosphoric, and sulfonic.

92. The composition of any one of embodiments 82 to 91, wherein the solid support comprises silicon, aluminum, germanium, boron, or phosphorous atoms, or any combination thereof.

93. The composition of any one of embodiments 82 to 92, wherein the solid support comprises a moiety having a structure of Formula M-Y—Z, wherein:
M is silica, alumina, silica-alumina, $TiO_2$, $ZrO_2$, $Nb_2O_5$, or any combinations thereof;
Y is silicon, aluminum, germanium, boron, or phosphorous; and
Z is the linker;
wherein Z is attached to the amine moiety, and
wherein Y is attached to M and Z.

94. The composition of any one of embodiments 66 to 93, wherein the amine catalyst comprises an amine moiety, wherein the amine moiety comprises:

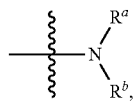

wherein $R^a$ and $R^b$ at each occurrence are independently H, alkyl, carbocyclyl, heterocyclyl, or ether, or any combinations thereof;
wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;

or $R^a$ and $R^b$ are taken together with the nitrogen atom to which they are both attached to form a heterocycle,
wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.

95. The composition of embodiment 94, wherein $R^a$ and $R^b$ are taken together with the nitrogen atom to which they are both attached to form a heterocycle, wherein the heterocycle comprises:
   1 to 8 heteroatoms;
   wherein the heteroatoms are independently selected from the group consisting of N, O, S, and P;
   1 to 30 carbon atoms; and
   the heterocycle is unsubstituted or substituted with one or more substituents selected from the group consisting of alkyl, hydroxyl, amine, oxo, carboxyl, imine, carbocyclyl, heterocyclyl, halo, ether, and thioether.

96. The composition of any one of embodiments 66 to 93, wherein the amine catalyst comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

97. The composition of embodiment 96, wherein the heterocycle comprises 1 to 30 carbon atoms and 1 to 8 heteroatoms, wherein the heteroatoms are independently selected from the group consisting of N, O, S, and P.

98. The composition of any one of embodiments 82 to 97, wherein the linker comprises:
   -alkyl-, -aliphatic-, -aryl-, -carbocycle-, -heterocycle-, -sulfone-, or -ether-, or any combinations thereof;
   wherein the -alkyl-, -aliphatic-, -aryl-, -carbocycle-, -heterocycle-, -sulfone-, -ether- are unsubstituted or substituted with one or more substituents independently selected from the group consisting of alkyl, hydroxyl, amine, oxo, carboxyl, imine, carbocyclyl, and heterocyclyl.

99. The composition of any one of embodiments 82 to 98, wherein the linker comprises at least three linear chain atoms.

100. The composition of any one of embodiments 82 to 99, wherein the linker comprises 3 to 30 linear chain atoms.

101. The composition of any one of embodiments 82 to 100, wherein the linker comprises 3 to 20 linear chain atoms.

102. The composition of any one of embodiments 66 to 101, wherein the amine catalyst comprises a secondary amine.

103. The composition of any one of embodiments 82 to 101, wherein the amine moiety is selected from the group consisting of:

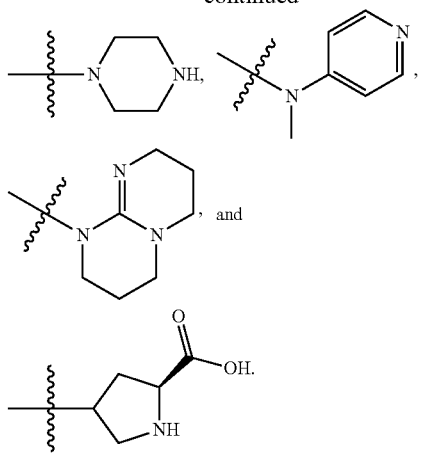

104. The composition of any one of embodiments 82 to 101, or 103, wherein the amine catalyst comprises:

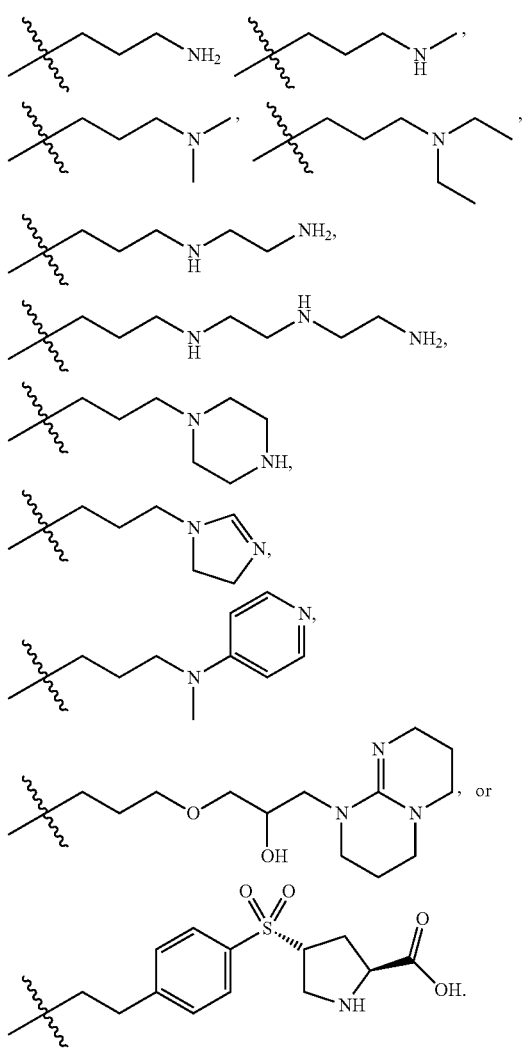

105. The composition of any one of embodiments 82 to 101, wherein the linker comprises:

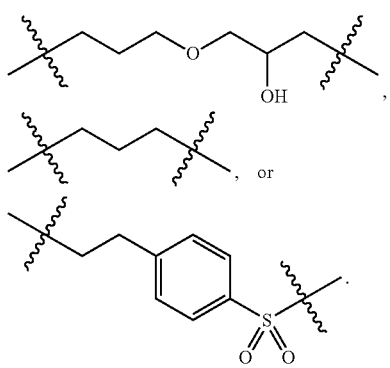

106. The composition of any one of embodiments 66 to 105, further comprising an acid.
107. The composition of embodiment 106, wherein the amine catalyst is an unsupported amine catalyst.
108. The composition of embodiment 106 or 107, wherein the amine catalyst is selected from the group consisting of diethylamine, piperazine, pyrrolidine, proline, imidazole, pyridine, triazabicyclodecene, and 4-dimethylaminopyridine.
109. The composition of any one of embodiments 106 to 108, wherein the amine catalyst is selected from the group consisting of pyrrolidine, piperazine, and proline.
110. The composition of embodiment 106, wherein the acid is supported or unsupported.
111. The composition of embodiment 110, wherein the acid is supported on a support comprising silica, silica-alumina, alumina, TiO$_2$, ZrO$_2$, Nb$_2$O$_5$, or any combinations thereof.
112. The composition of any one of 106 to 110, wherein the acid is selected from the group consisting of acetic acid, benzoic acid, terephthalic acid, phthalic acid, isophthalic acid, adipic acid, succinic acid, oxalic acid, pimelic acid, valeric acid, muconic acid, mucic acid, toluic acid, citric acid, and mineral acids, or any combinations thereof.
113. The composition of any one of embodiments 106 to 112, wherein the acid comprises a carboxylic acid moiety.
114. The composition of any one of embodiments 106 to 110, wherein the acid is selected from the group consisting of acetic acid and benzoic acid.
115. The composition of any one of embodiments 66 to 114, further comprising a solvent.
116. The composition of embodiment 115, wherein the solvent comprises toluene, xylenes, dimethyl sulfoxide, dimethylfuran, tetrahydrofuran, alkanes, or any combination thereof.
117. The composition of embodiment 115 or 116, wherein the solvent comprises toluene.
118. The composition of any one of embodiments 66 to 117, further comprising a fermentation product mixture.
119. A composition, comprising:
    a fossil fuel; and
    an alkane of embodiment 64, or an alcohol of embodiment 65, or a mixture thereof.
120. A fuel or a lubricant, comprising:
    at least one alkane produced according to the method of embodiment 61, or at least one alcohol produced according to the method of embodiment 62, or a mixture thereof.

EXAMPLES

The following Examples are merely illustrative and are not meant to limit any aspects of the present disclosure in any way.

Unless otherwise specified, silica-alumina (BET=470 m$^2$g$^{-1}$, average pore diameter: ~8 nm), silica (surface area: 500 m$^2$g$^{-1}$, average pore diameter: ~6 nm), and other chemicals used in the Examples described herein were purchased from either Sigma-Aldrich or Gelest, Inc. and used as received without further purification.

Example 1

Preparation and Characterization of Silica-Alumina Supported Amine Catalysts

This Example demonstrates the preparation and characterization of the silica-alumina supported amine catalysts listed in Table 1.

TABLE 1

| Entry | Catalyst Name | Amine Moiety |
|---|---|---|
| 1 | Si—Al—NH$_2$ | |
| 2 | Si—Al—NHR | |
| 3 | Si—Al—NR$_2$ | |
| 4 | Si—Al—NEt—NH$_2$ | |
| 5 | Si—Al—(NEt)$_2$—NH$_2$ | |

TABLE 1-continued

| Entry | Catalyst Name | Amine Moiety |
|---|---|---|
| 6 | Si—Al-Piperazine | |
| 7 | Si—Al-Imidazole | |
| 8 | Si—Al-DMAP | |
| 9 | Si—Al-TBD | |
| 10 | Si—Al-Proline | |

Preparation of Si—Al Supported Catalysts:

The following procedure provides a method that can be employed to prepare supported amine catalysts of formula Si—Al—NR'R", wherein R' and R" are independently H, alkyl or imidazolyl (e.g., Entries 1 to 5, 7). Silica-alumina (Si—Al) support material was calcined in air at 773 K for 6 h and then stored in vacuum prior to use. Typically, the post grafting of organoamines onto Si—Al was accomplished by stirring 1 g of Si—Al using an amine reagent (~1-4 mmol) in 100 ml of ethanol at 343 K for 16 h under inert conditions. The hot solution was then cooled down to room temperature, filtered, washed with copious amounts of ethanol, and then dried in vacuum oven at 373 K for overnight. The choice of amine reagent used in the grafting step described above determines the linker length and the amine moiety of the resulting supported amine catalyst. For example, to prepare the supported amine catalyst Entry 1, the calcined Si—Al is stirred with 3-aminopropyltrimethoxysilane. To prepare the supported amine catalyst Entry 2, the calcined Si—Al is stirred with 3-(N-methylaminopropyl)trimethoxysilane.

Preparation of Si—Al Supported Piperazine Catalysts (e.g., Entry 6):

2 g of vacuum dried Si—Al support was allowed to react with (3-chloropropyl)triethoxysilane (4 mmol) in dry toluene at reflux for 24 h. The chloropropylated Si—Al support (1.0 g) was allowed to react with piperazine (~2 mmol) and sodium hydride (4.5 mmol) in 30 mL of dry THF under $N_2$ atmosphere at 0° C. The solution was stirred for additional 1 h at room temperature and the solution was stirred further for 16 h at 70° C. The solution was then filtered, washed with copious amounts of THF and ethanol and dried in vacuo, to give the supported piperazine catalyst Entry 6. Other supported piperazine catalysts can be prepared using this procedure by replacing the (3-chloropropyl)triethoxysilane with an appropriate compound. For example, to prepare a supported a piperazine catalyst with a longer linker, the (3-chloropropyl)triethoxysilane could be substituted with (3-chlorobutyl)triethoxysilane.

Preparation of Si—Al Supported 4-(dimethylaminopyridine) (DMAP) Catalysts (e.g., Entry 8):

4-(N-methylamino)pyridine (~2 mmol) in 70 mL of dry tetrahydrofuran (THF) was added drop wise to a suspension of sodium hydride (4.5 mmol) in 30 mL of dry THF under $N_2$ atmosphere at 0° C. The solution was stirred for additional 2 h at room temperature. Afterwards, 1 g of chloropropylated Si—Al support containing was slowly added into the reaction mixture and the solution was stirred further for 16 h at 70° C. The solution was then filtered, washed with copious amounts of THF and ethanol and dried in vacuo, to give supported DMAP catalyst Entry 8. Other supported DMAP catalysts can be prepared using this procedure by replacing the (3-chloropropyl)triethoxysilane with an appropriate compound. For example, to prepare a supported a DMAP catalyst with a longer linker, the (3-chloropropyl)triethoxysilane could be substituted with (3-chlorobutyl)triethoxysilane.

Preparation of Si—Al Supported Triazabicyclodecene (TBD) Catalyst (e.g., Entry 9):

2 g of vacuum dried Si—Al support was allowed to react with (3-glycidoxypropyl)trimethoxysilane (4 mmol) in dry toluene at reflux for 24 h. The glycidylated Si—Al support (1.0 g) was allowed to react with 1,5,7-triazabicyclo[4.4.0]undec-3-ene (TBD, ~2 mmol) in toluene (30 mL) at 300 K for 15 h, and excess TBD was removed by soxhlet extraction with dichloromethane and the catalyst was stored under vacuum. Other supported TBD catalysts can be prepared using this procedure by replacing the (3-glycidoxypropyl)trimethoxysilane with an appropriate compound. For example, to prepare a supported a TBD catalyst with a longer linker, the (3-glycidoxypropyl)trimethoxysilane could be substituted with (3-glycidoxybutyl)trimethoxysilane.

Preparation of Si—Al Supported Proline Catalysts (e.g., Entry 10):

3 g of vacuum dried Si—Al support was allowed to react with 4-[2-(trimethoxysilyl)ethyl]benzene-1-sulfonyl chloride (3 mmol) in dry toluene at reflux for 12 h. The —SO$_2$Cl containing Si—Al support (1.0 g) was allowed to react with the dropwise addition of trans-4-hydroxy-L-proline (~2 mmol) at 60° C., under stirring and the mixture was stirred at 60° C. for 3 h under N$_2$. The solid supported proline catalyst was separated, washed with ethanol, diethyl ether and finally dried under reduced pressure.

Infrared Characterization:

Infrared spectra were acquired using a Thermo Scientific Nicolet 6700 FTIR spectrometer equipped with a liquid nitrogen cooled MCT detector. Each spectrum was obtained by averaging 32 scans taken with 1 cm$^{-1}$ resolution. A 0.05 g portion of Si—Al-supported amine was pressed into a 20 mm-diameter pellet (<1 mm thick) and placed into a custom-built transmission cell equipped with CaF$_2$ windows, a K-type thermocouple for temperature control, and resistive cartridge heaters.

Nuclear Magnetic Resonance (NMR) Characterization:

Solid-state $^{13}$C CP MAS NMR and $^{29}$Si MAS NMR experiments were performed on a Bruker Avance I 500 MHz spectrometer equipped with a H/X double resonance magic angle spinning probe which uses 4 mm O.D. rotors. $^{13}$C cross-polarization, tuned to 125.79 MHz, MAS NMR experiments were obtained using a 1H 90° pulse width of 4.2 μs, 2 ms contact time, 60 kHz decoupling field and 2-5 s recycle delay at a spinning rate of 7-13 kHz. All $^{13}$C spectra were referenced against the chemical shifts of adamantane at 38.48 and 29.45 ppm. The $^{29}$Si with $^1$H decoupling MAS NMR spectra were acquired at 99.37 MHz, using a $^{29}$Si 90° pulse width of 7.5 μs, recycle delay of 600 s, and spinning rate of 10-11 kHz. All $^{29}$Si spectra were referenced against polydimethylsiloxane at −22 ppm (relative to TMS at 0 ppm). The resolution obtained in the $^{29}$Si NMR spectra was sufficient for accurate peak assignments, and the relative peak area of each site was obtained by the curve-fitting, using a series of Gaussian peaks.

Figure 4A:
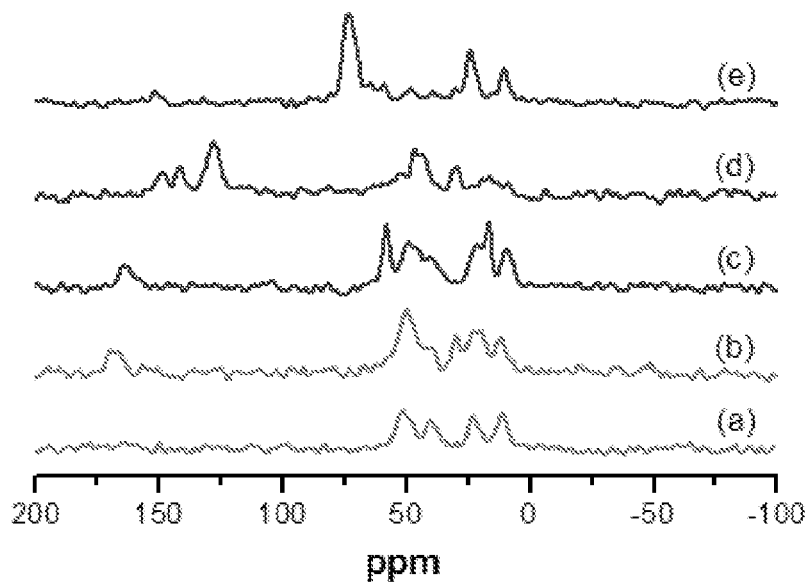
FIG. 4A depicts solid-state $^{13}$C CP magic-angle spinning (MAS) nuclear magnetic resonance (NMR) spectra of silica-alumina supported amine catalysts, wherein the catalyst includes (a) —NHCH$_2$CH$_2$NH$_2$, (b) —(NHCH$_2$CH$_2$)$_2$NH$_2$, (c) imidazole moiety, (d) piperazine moiety, or (e) triazabicyclodecene moiety.
Figure 4B:
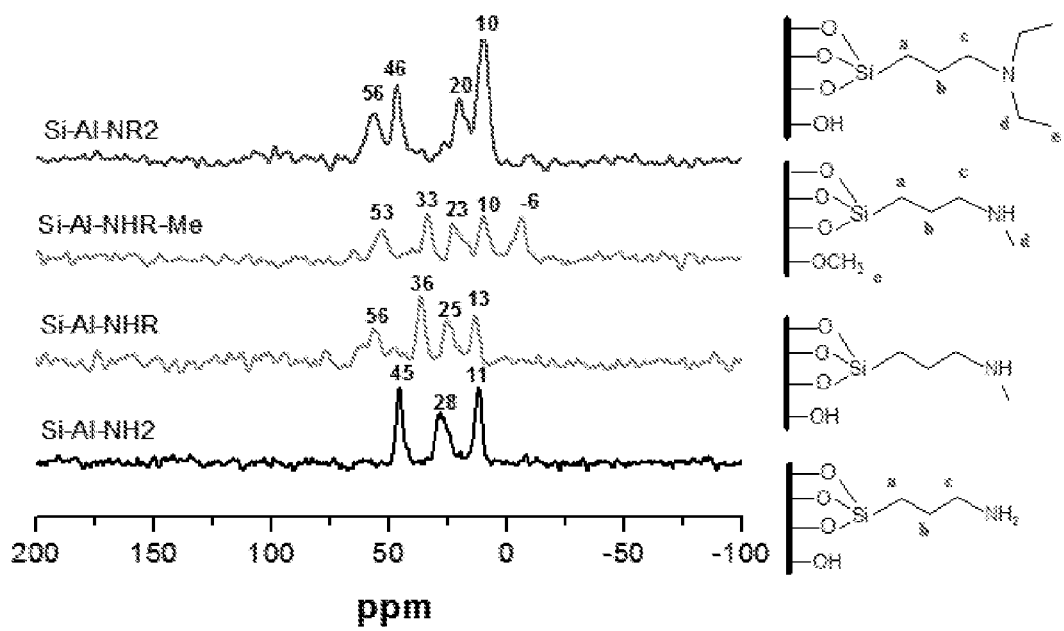
FIG. 4B depicts solid-state $^{13}$C CP MAS NMR spectra of silica-alumina supported amine catalysts, wherein the numbers above the spectra refer to the approximate spectral shift of the corresponding peaks.
Figure 5A:
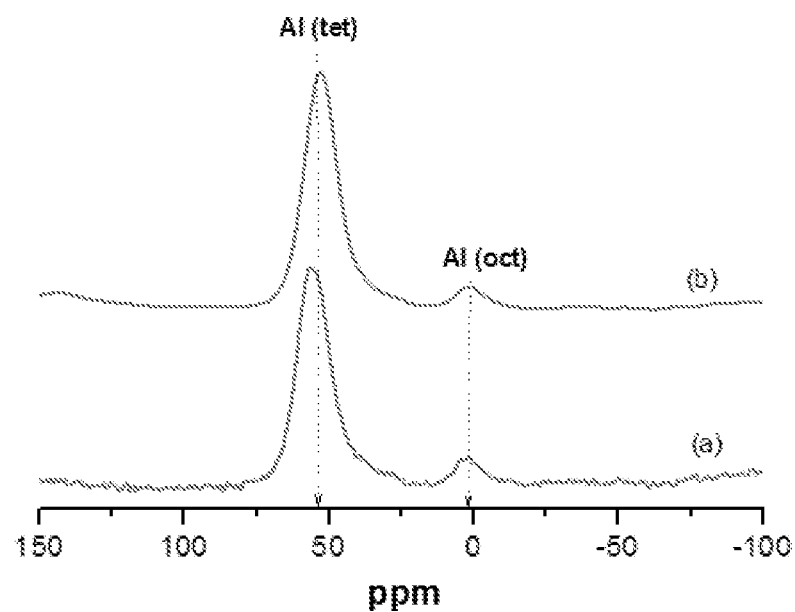
FIG. 5A depicts solid-state $^{27}$Al MAS NMR spectra of (a) silica-alumina and (b) an amine catalyst supported on silica-alumina.
Figure 5B:
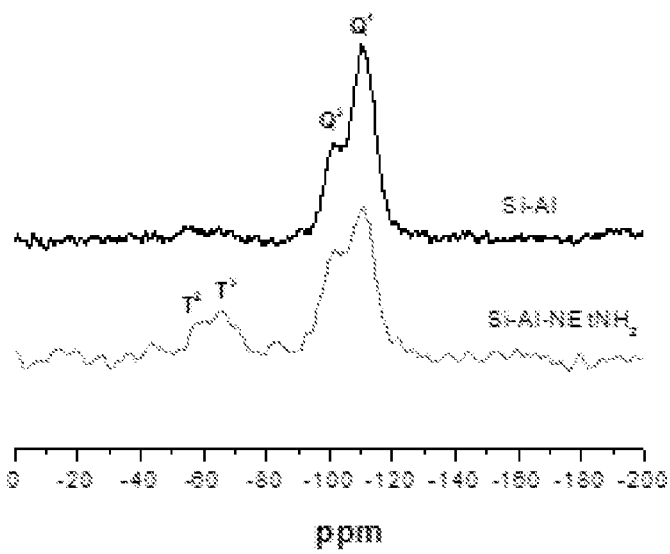
FIG. 5B depicts solid-state $^{29}$Si MAS NMR spectra of silica-alumina and an amine catalyst supported on silica-alumina.

Solid-state $^{13}$C magic-angle spinning (MAS) NMR confirmed the successful grafting of the respective organosilanes on the Si—Al surfaces. FIG. 4 depicts the solid-state $^{13}$C MAS NMR spectra of some of the alumina-supported amine catalysts prepared according to the procedure set forth above. The observed chemical shifts of the organic groups agree well with those of the corresponding organosilane precursors measured in solution. $^{29}$Si MAS NMR further confirmed the presence of organic functional groups grafted on the Si—Al support. FIG. 5 depicts the $^{29}$Si MAS NMR spectra of some of the alumina-supported amine catalysts prepared according to the procedure set forth above. Peaks at δ=−110, −100, −90, −65, and −55 ppm were assigned to Q$^4$(Si(OSi)$_4$), Q$^3$(Si(OH)(OSi)$_3$), Q$^2$(Si(OH)$_2$(OSi)$_2$), T$^3$(SiR(OSi)$_3$), and T$^2$(Si(OH)R(OSi)$_2$) sites, respectively. Presence of peaks at −65 and −55 ppm indicate the formation of T″ sites [RSi(OEt)$_n$(OSi)$_{3-n}$] and a higher T$^3$/T$^2$ ratio from the $^{29}$Si MAS NMR confirms a strong covalent linkage between the organocatalysts and the Si—Al support.

Example 2

Dimerization of Heptan-2-one by Different Silica-Alumina Supported Amine Catalysts This Example demonstrates the use of different silica-alumina supported amine catalysts to dimerize heptan-2-one. The silica-alumina supported amine catalysts were prepared according to the procedure set forth in Example 1 above.

Reaction Studies:

To a 12 mL Q-tube containing a stir bar, a supported amine catalyst chosen from those listed in Table 2 below (~80-100 mg), and heptan-2-one (2 mmol) was added. The Q-tube was sealed and the reaction mixture was stirred for 12 h at 443 K in a pre-heated metal block. The reaction mixture was cooled to room temperature and dodecane was added as an internal standard. The reaction mixture was diluted with tetrahydrofuran and gas chromatography analysis of the reaction mixture was carried out. The dimerization yield obtained with each catalyst is summarized in Table 2 below.

TABLE 2

| Entry | Catalyst Name | Amine Moiety | Dimerization Yield (%) |
|---|---|---|---|
| 1 | Si—Al—NH$_2$ | (structure: propyl-NH$_2$) | 31 |
| 2 | Si—Al—NHR | (structure: propyl-NH-methyl) | 48 |
| 3 | Si—Al—NR$_2$ | (structure: propyl-N(methyl)$_2$) | 24 |
| 4 | Si—Al—NEt—NH$_2$ | (structure: propyl-NH-CH$_2$CH$_2$-NH$_2$) | 53 |

TABLE 2-continued

| Entry | Catalyst Name | Amine Moiety | Dimerization Yield (%) |
|---|---|---|---|
| 5 | Si—Al—(NEt)₂—NH₂ | | 34 |
| 6 | Si—Al-Piperazine | | 29 |
| 7 | Si—Al-Imidazole | | 25 |
| 8 | Si—Al-DMAP | | 2 |
| 9 | Si—Al-TBD | | 3 |
| 10 | Si—Al-Proline | | 51 |

Screening of various amine catalysts, under neat conditions, for the dimerization of heptan-2-one showed that Si—Al supported secondary amines are more active than primary amines, whereas tertiary amines are less active. The only products observed under any of the conditions investigated were the $C_{14}$ dimerized product. Under equal concentration of amine groups, Si—Al-supported secondary amines (Si—Al—NHR) showed a similar conversion to that of a supported proline sample. This result suggests that supporting secondary amines on silica-alumina can mimic the constrained site isolation in proline catalysts.

The catalysts in Table 1 were all observed to produce at least some dimerized product. The catalyst prepared with a diamine (Si—Al—NEt-NH₂) showed a slightly better activity than the Si—Al—NHR catalyst, whereas the catalyst prepared with a diamine showed approximately two times greater activity than the catalyst prepared with a triamine catalyst such as Si—Al (Si—Al—(NEt)₂NH₂).

Example 3

Substrate Scope of Silica-Alumina Diamine Catalyst

This Example demonstrates the use of a supported diamine catalyst to catalyze the dimerization of methyl ketones ranging from 4 to 15 carbons.

The silica-alumina supported diamine catalyst of Entry 4 (Si—Al—NEt-NH₂) in Table 2 was used in this Example and prepared according to the procedure set forth in Example 1. The methyl ketone reactions were carried out according to the procedure set forth in Example 2.

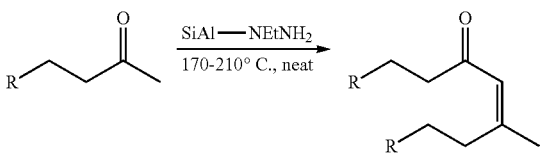

C8
2-C5: 20% conv.
>95% selectivity

C10
2-C5: 72% conv.
>95% selectivity

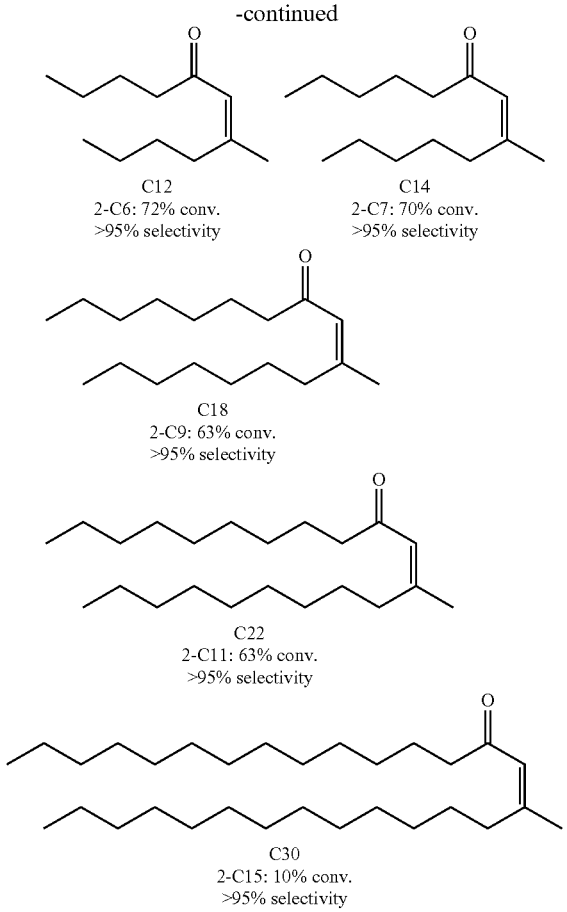

The dimerization of methyl ketones was examined for ketones containing 4-15 carbon atoms using the Si—Al—NEtNH$_2$ catalyst. It should be understood that when a methyl ketone dimerizes, the product has twice the number of carbons than the starting methyl ketone. A C$_5$ methyl ketone will dimerize to produce a C$_{10}$ ketone product. All substrates produced dimers of the ketones and the yields were greater than 60% for C$_5$, C$_6$, C$_7$, C$_9$, and C$_{11}$ ketones substrate (e.g., the starting ketone in the reaction scheme above). The C$_{15}$ substrate showed a lower product yield, which may be due to its long carbon chain length and difficulty in diffusing into the narrow pores of the support. Without wishing to be bound by any theory, these results suggest that the reaction rate may be limited by the molecular diffusion of the reactants and products within the pore channels (~8 nm) of the Si—Al support when longer chain ketone substrates are used.

Example 4

Effect of Water on Methyl Ketone Dimerization

This Example demonstrates the use of a silica-alumina supported amine catalyst to catalyze the dimerization of heptan-2-one in the presence of added water.

The silica-alumina supported diamine catalyst of Entry 4 (Si—Al—NEt-NH$_2$) in Table 2 was used in this Example and prepared according to the procedure set forth in Example 1. The reaction studies were carried out and analyzed as according to the procedure set forth in Example 2, using a 12 mL Q-tube, 100 mg of catalyst, 228 mg of heptan-2-one, a reaction time of 16 h, a reaction temperature of 443 K, and the addition of 0 to 114 mg water.

Figure 2:
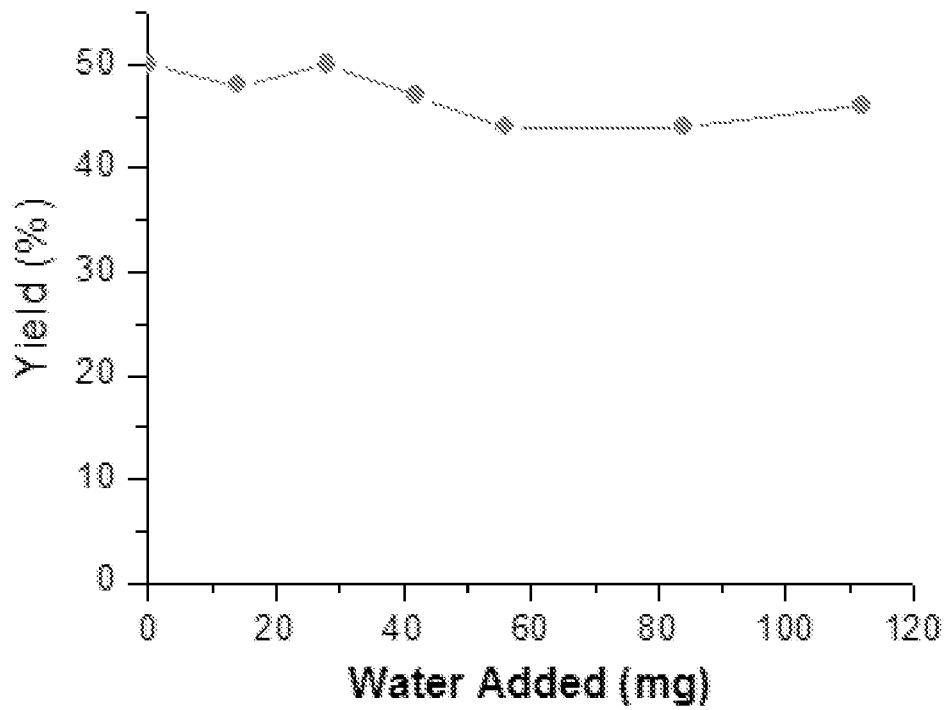
FIG. 2 is a graph depicting the effect of varying the concentration of water on the dimerization of heptan-2-one in the presence of an amine catalyst. Each reaction was performed in a 12 mL Q-tube with 228 mg of heptan-2-one, 100 mg of amine catalyst, and between 0 and 120 mg of water, at a temperature of 443 K for 16 h.

The dimerization yield of each reaction is summarized in FIG. 2. The Si—Al supported amine catalyst is water tolerant and retains similar catalytic activity even after 50% water in the reaction mixture. The results of this Example demonstrate the use of supported organocatalysts in upgrading of biomass derived intermediates to give higher molecular weight compounds.

Example 5

Time on Stream (TOS) Studies

This Example demonstrates the performance over time of a silica-alumina supported amine catalyst in the dimerization of heptan-2-one, as compared to a hydrotalcite catalyst. As used herein, "time on stream" refers to the amount of time a catalyst has been exposed to a continuously introduced flow of reactant.

Supported Amine Catalyst TOS Study:

The silica-alumina supported diamine catalyst Entry 4 (Si—Al—NEt-NH$_2$) in Table 2 was prepared according to the procedure set forth in Example 1. Gas-phase self-condensation of butan-2-one was performed in a 6.35 mm OD (~4 mm ID) quartz tube containing an expanded section (~12.7 mm OD, ~20 mm length). The reactor was packed with quartz wool above and below the catalyst bed to hold the catalyst in place. The feed to the reactor consisted of He and 0.2 mol % butan-2-one. The catalysts were pretreated at 473 K for 1 h before passing the feed. Experiments were carried out at 473 K, total gas pressures of 1 atm, total gas flow rate of 150 cm$^3$ min$^{-1}$. Reaction products were analyzed using an Agilent 6890N gas chromatograph containing a bonded and crosslinked (5%-phenyl)-methylpolysiloxane capillary column (Agilent, HP-1) connected to a flame ionization detector.

Hydrotalcite Catalyst TOS Study:

Hydrotalcite was purchased from Sigma-Aldrich and calcined at 823 K for 5 h before use. Gas-phase self-condensation of butan-2-one was performed following the procedure set forth for the supported amine catalyst TOS study above, using 100 mg of hydrotalcite as the catalyst.

Figure 3A:
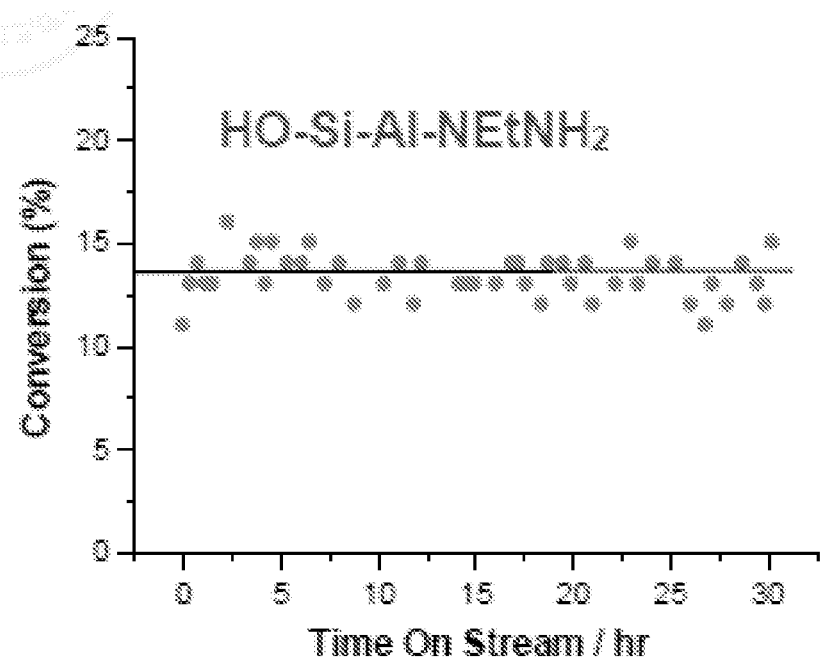
FIG. 3A is a graph depicting the catalytic activity over time of an amine catalyst in the gas-phase condensation of butan-2-one. The reaction was performed in a 6.35 mm OD (~4 mm ID) quartz tube containing an expanded section (~12.7 mm OD, ~20 mm length). The feed to the reactor consisted of He with 0.2 mol % butan-2-one. Experiments were carried out at 473 K, total gas pressures of 1 atm, total gas flow rate of 150 cm$^3$ min$^{-1}$, with 100 mg of amine catalyst with an amine loading of 0.4 —NHR/nm$^2$.
Figure 3B:
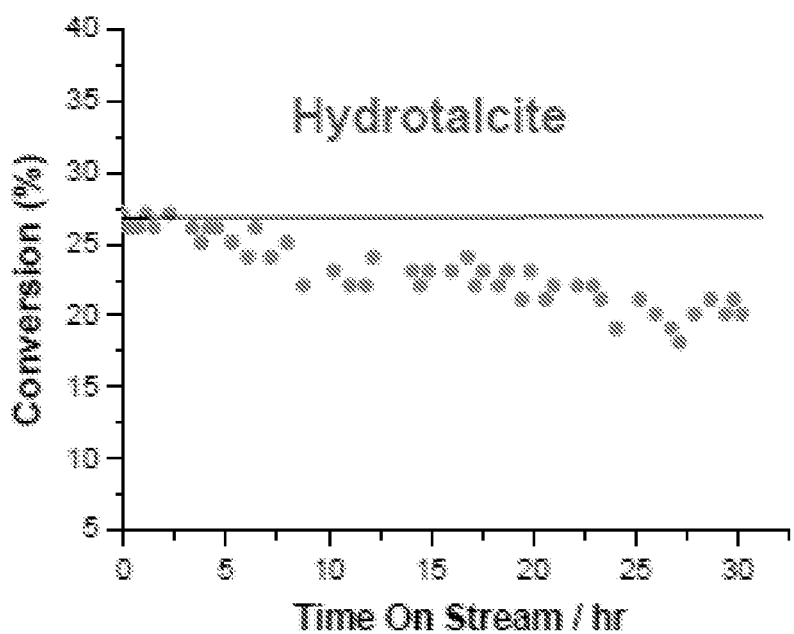
FIG. 3B is a graph depicting the catalytic activity over time of a hydrotalcite catalyst in the dimerization of butan-2-one. The reaction was performed in a 6.35 mm OD (~4 mm ID) quartz tube containing an expanded section (~12.7 mm OD, ~20 mm length). The feed to the reactor consisted of He with 0.2 mol % butan-2-one. Experiments were carried out at 473 K, total gas pressures of 1 atm, total gas flow rate of 150 cm$^3$ min$^{-1}$, with 100 mg of hydrotalcite catalyst.

FIGS. 3A and 3B summarize the results of the Time on Stream (TOS) experiments. The results FIG. 3A of the TOS studies of the supported amine catalyst demonstrate that the amine catalyst were stable up to 30 h and did not exhibit significant deactivation. The results in FIG. 3B of the TOS studies of the hydrotalcite catalyst demonstrate the hydrotalcite catalyst exhibited a decrease in conversion over time.

Results showed that the conversion yield in the presence of amine catalyst was about half that of the hydrotalcite catalyst. Without wishing to be bound by any theory, the lower conversion with the amine catalyst may be due to the lower basicity of the amine groups and to the low density of amine groups on the support material. The hydrotalcite catalyst showed deactivation during time on stream studies, with the conversion decreasing by about half after 30 h. The amine catalyst was stable during the reaction over 30 h. Without wishing to be bound by any theory, the stability over time of the amine catalyst may be related to the water tolerance of the organocatalysts. This result is consistent with the water inhibition studies carried out in the liquid phase, in which the supported amine catalyst showed similar conversion rates in the presence of additional water.

Example 6

Heptan-2-one Dimerization by Unsupported Amine Catalysts

This Example demonstrates catalysis of heptan-2-one dimerization using unsupported amine catalysts in the additional presence of an acid.

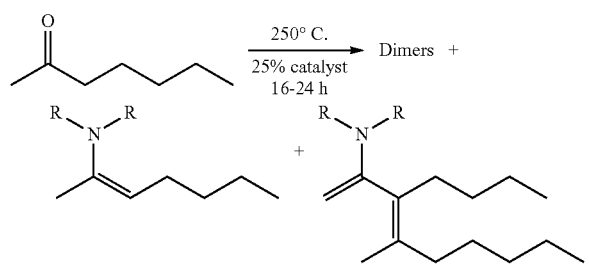

The R groups refer to substituents on the amine catalyst.

Reaction Studies:

To a 12 mL Q-tube equipped with a stir bar, the amine catalyst (1.0 mmol), the organic acid (1.0 mmol), 2-heptanone (4.0 mmol) and an internal standard (dodecane, 80 mg) were added. The Q-tube was sealed using a PTFE-faced silicone septa and a QianCap. It was then added to an aluminum block preheated to 523 K and stirred for 24 h. The reaction mixture was then cooled to room temperature, diluted with dichloromethane and analyzed by gas chromatography. The dimerization yield obtained with each catalyst system is summarized in Table 3.

Upon screening several different organoamine catalysts it was observed that these catalysts primarily yield dimerized product, unreacted 2-heptanone and the enamine reaction intermediate. This procedure produced dimerized product when using one of a variety of secondary alkyl amine catalysts and acetic acid. Other organic acids may be used for this transformation. For example, when benzoic acid is used, dimer products are formed.

TABLE 3

| Amine | Acid | Recovered 2-heptanone (%) | Dimerization Yield (%) |
|---|---|---|---|
| diethylamine | acetic acid | 40 | 30 |
| proline | acetic acid | 54 | 21 |
| piperidine | acetic acid | 30 | 36 |
| pyrrolidine | acetic acid | 39 | 25 |
| pyrrolidine | benzoic acid | 9 | 15 |

Example 7

Dimerization of Heptan-2-one by Supported Amine Catalysts with the Support Modified with Additional Acid Groups This Example demonstrates the use of a supported amine catalyst in the dimerization of heptan-2-one wherein the support of the amine catalyst has been modified with additional acid groups.

Preparation of Si—Al Supported Amine and Organic Acid Catalysts:

1 g of silica-alumina (Si—Al) support material was stirred with N-(2-aminoethyl)3-aminopropyltrimethoxy silane (~1 mmol) followed by the slow addition of 4-[2-(trimethoxysilyl)ethyl]benzene sulfonic acid (~1 mmol) in 100 ml of ethanol at 343 K for 16 h. The hot solution was then cooled down to room temperature, filtered, washed with copious amounts of water and ethanol, and then dried in a vacuum oven at 373 K for overnight. A similar synthesis procedure was followed to obtain Si—Al supported amine catalysts wherein the support was further modified with phosphoric acid or carboxylic acid groups.

The dimerization of heptan-2-one was carried out with each catalyst according to the procedure set forth in Example 2.

TABLE 4

| Alkyl Organic Acid | Acid Moiety | Acid pKa | Dimerization Yield (%) |
|---|---|---|---|
| (aryl-SO$_3$H) | sulfonic acid | −2 | 17 |
| (alkyl-PO$_3$H$_2$) | phosphoric acid | 3 | 21 |
| (alkyl-COOH) | carboxylic acid | 5 | 29 |
| Si(OH)Al | hydroxyl group | 8 | 53 |

The acid-base pair effect was investigated by preparing supported amines in which the support was also modified with various alkyl organic acids, including a sulfonic acid (pKa=−2), phosphoric acid (pKa=3) and carboxylic acid (pKa=5). The catalyst activity was found to decrease with decreasing pKa of the acid groups. It was also observed that the cooperative interactions of amines with weakly acidic silanols/aluminols are much more effective than organic acids. Without wishing to be bound by any theory, this result suggests that the equilibrium shifts towards the protonated acid-base pair when acidic protons lie in close proximity to the amine groups. Strong acids in close proximity may protonate the nitrogen to lower its nucleophilicity and slow down the formation of enamines.

Example 8

Effect of Solid Support Identity and Linker Length on Dimerization of Heptan-2-one by Amine Catalysts This Example demonstrates how catalytic activity of a silica-alumina supported secondary amine catalyst is affected by the length of the linker. This Example also demonstrates how the identity of the heterogeneous support may affect the catalytic activity of a supported amine catalyst.

Preparation of Supported Secondary Amine Catalysts:

The supported amine catalysts were prepared following the procedure set forth in Example 1, such that they contained a secondary N-methylamino moiety and an alkyl linker of the length designated in Table 5. The silica ($SiO_2$) supported amine catalyst was prepared using silica instead of silica-alumina as the solid support. Silylation of amine catalysts supported by Si—Al was performed by dispersing 1 g of the catalyst in 25 mL of dry toluene followed by the addition of 3 mmol of methyl trimethoxysilane and stirring at 373 K for 12 h under an inert atmosphere.

Reaction Studies:

Dimerization studies of heptan-2-one by supported amine catalysts were carried out following the procedure set forth in Example 2. Reactions with unmodified silica-alumina alone, the unsupported amine (N-methylbutyl amine) alone, or a combination of unmodified silica-alumina and the unsupported amine (N-methylbutyl amine) were carried out following a procedure analogous to that followed for supported amine catalysts.

TABLE 5

| Solid Support | Amine Catalyst | State of Amine | Dimerization Yield (%) |
|---|---|---|---|
| Si—Al | none | — | 0 |
| none | N-methylbutylamine | unsupported | 0 |
| Si—Al | N-methylbutylamine | unsupported | 27 |
| Si—Al | (propyl linker, NHCH₃) | supported | 48 |

TABLE 6

| Solid Support | Linker Length | Dimerization Yield (%) |
|---|---|---|
| Si—Al | $C_5$ | 34 |
| Si—Al | $C_3$ | 48 |
| Si—Al | $C_1$ | 3 |
| $SiO_2$ | $C_3$ | 15 |
| Sil-Si—Al | $C_3$ | 9 |

The amine moiety for all catalysts described in Table 6 is —$NHCH_3$.

Table 5 summarizes the results of the unsupported catalyst experiments. Table 6 summarizes the results of the linker length and solid support identity experiments.

No dimerized product was observed to be produced in the control reactions carried out using the unmodified Si—Al support alone or an unsupported amine (N-methylbutylamine) alone. The use of combination of Si—Al and an unsupported amine (N-methylbutylamine) was observed to produce a dimerized product, although the yield of such dimerized product was lower than the use of an acid-base bifunctional Si—Al—NHR catalyst.

These results suggest that the effect of having the immobilized acid and base groups in close proximity may result in co-operative catalytic enhancement. Further support for these observations was obtained by noting the absence of activity for Si—Al—$C_1$—NHR, a catalyst in which the linker for the amine group contains only one carbon atom. Similarly, the supported amine catalyst Si—Al—$C_5$—NHR showed a ~30% decrease in activity than the Si—Al—$C_3$—NHR catalyst. Therefore, amine groups flexible enough to work cooperatively with the acidic hydroxyl groups but spaced far enough from these groups may avoid mutual neutralization of the acid and base groups. Blocking the silanol/aluminol groups by silylation using trimethoxysilane unexpectedly decreased catalyst activity by five-fold giving further evidence that the acidic sites may work co-operatively with the amines in the selective dimerization reaction of methyl ketones. The Si—Al supported amine unexpectedly showed a three-fold higher conversion than the corresponding silica supported amine catalyst. The improved catalytic activity for the amine grafted Si—Al compared to that of amorphous silica suggests that the Brønsted acidity of the support may play an important role in enhancing the catalytic activity of the heterogenized amine samples.

Example 9

Effect of Amine Density and Temperature on Dimerization Yield

This Example demonstrates how changing the amine density of the solid supported catalyst, the reaction temperature, or the total catalyst loading can affect dimerization yield.

The silica-alumina supported amine catalysts used in these experiments is Entry 4 (Si—Al—NEt-$NH_2$) in Table 2, prepared following the procedure set forth in Example 1, varying the amine density of the catalyst by varying the amount of amine reagent added during catalyst preparation. The reactions were performed according to the procedure set forth in Example 2 with heptan-2-one, varying, the loading of the catalyst, the amine density of the catalyst, or the temperature of the reaction as described in Table 7.

TABLE 7

| Amine Density ($nm^{-2}$) | Catalyst Loading (mg) | Reaction Temperature (K) | Dimerization Yield (%) |
|---|---|---|---|
| 0.2 | 100 | 443 | 56 |
| 0.4 | 100 | 443 | 53 |
| 0.5 | 100 | 443 | 38 |
| 0.6 | 100 | 443 | 21 |

TABLE 8

| Catalyst Loading (mg) | Reaction Temperature (K) | Dimerization Yield (%) |
|---|---|---|
| 100 | 443 | 23 |
| 150 | 443 | 53 |
| 200 | 443 | 74 |

TABLE 8-continued

| Catalyst Loading (mg) | Reaction Temperature (K) | Dimerization Yield (%) |
|---|---|---|
| 100 | 423 | 15 |
| 100 | 443 | 23 |
| 100 | 473 | 72 |

Table 7 summarizes how varying amine density affects dimer yield. Table 8 summarizes how varying catalyst loading or reaction temperature affect dimerization yield.

Figure 7:
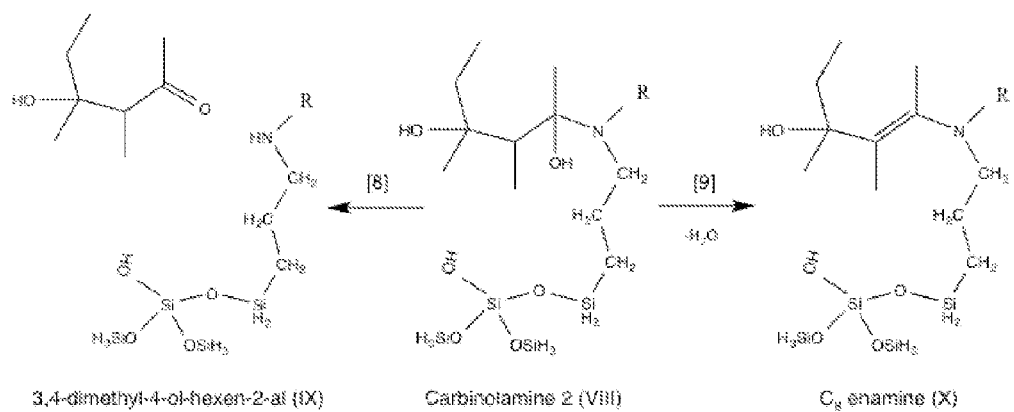
FIG. 7 depicts an exemplary reaction scheme showing the proposed branching point between butan-2-one dimerization and trimerization pathways.

The effect of varying the density of amines groups on the Si—Al surfaces was examined. As shown in Table 7, increasing amine content on the Si—Al surface decreased the catalytic activity. Stated another way, at low amine loading, an increase in co-operativity between basic sites and silanols/aluminols was achieved by preventing amine aggregation on the Si—Al support surface. Further experimentation revealed that the yield of dimer increased from 24% to 68% by increasing the mass of catalysts from 100 mg to 200 mg, as shown in Table 8. The product yield can be enhanced significantly, from 15% to 72%, by varying the reaction temperature from 423 K to 473 K. When the reaction was carried out using 100 mg of amine catalyst and at 443 K, only dimer products were observed. When the mass of catalyst increased to ~200 mg, or the temperature increased to 473 K, trimer products were observed in a dimer to trimer ratio of ~4:1. Without wishing to be bound by any theory, FIG. 7 depicts an exemplary reaction scheme showing the proposed branching point between butan-2-one dimerization and trimerization pathways, which may be similar to the dimerization and trimerization pathways of heptan-2-one.

Example 10

Dimerization of Heptan-2-one in the Presence and Absence of Solvent

This Example demonstrates how solvent affects the dimerization yield of a methyl ketone by a silica-alumina supported amine catalyst. The supported amine catalyst was prepared as described in Experiment 1. The catalyst used is Si—Al—NEt-NH$_2$ listed in Table 1. The dimerization of heptan-2-one was carried out as described in Experiment 2 at 443 K for 16 h, using 100 mg of supported catalyst and 2 mmol heptan-2-one, with either no solvent or with 5 mL of toluene added.

The dimerization yield under solvent-free conditions was 53%. The dimerization yield in the presence of added toluene was 51%.

Example 11

Characterization of Si—Al—NEtNH$_2$ During Butan-2-one Dimerization

Figure 9:
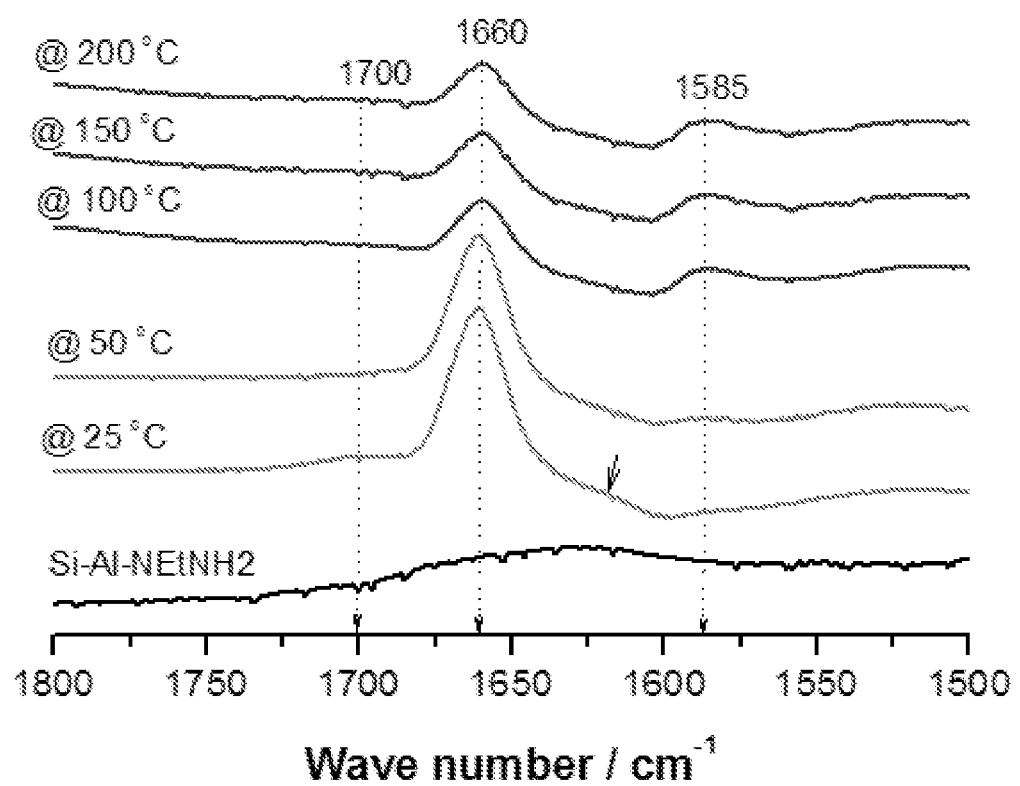
FIG. 9 depicts in situ Fourier transform infrared (FT-IR) spectra of an amine catalyst supported on silica-alumina at different reaction temperatures, in the presence of butan-2-one.

This Example demonstrates characterization of the reaction mechanism catalyzed by silica-alumina supported amine catalysts in the dimerization of methyl ketones, using in situ Fourier transform infrared (FT-IR) spectroscopy. The catalyst characterized was Si—Al—NEt-NH$_2$ listed in Table 1, prepared as described in Example 1. The FT-IR spectra obtained at different temperatures is shown in FIG. 9.

Figure 6A:
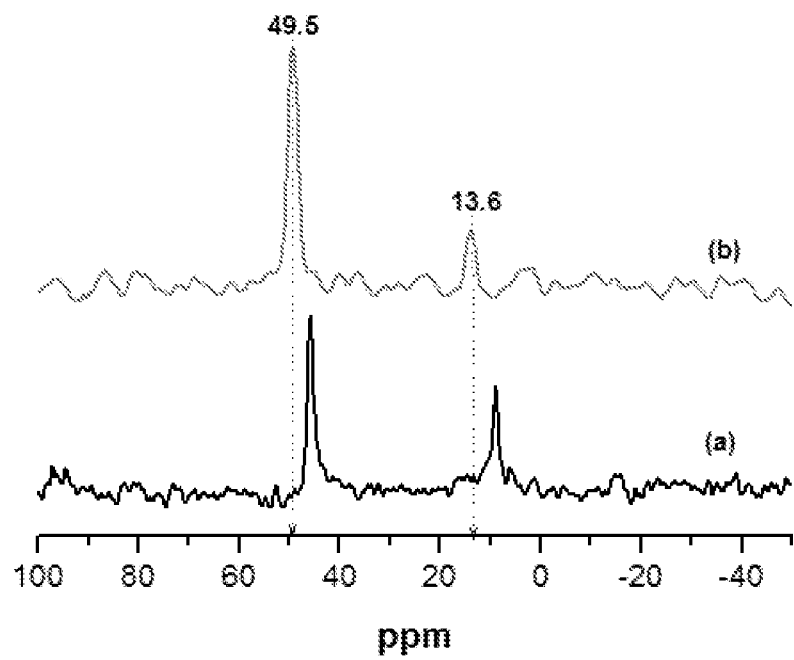
FIG. 6A depicts solid-state $^{13}$C CP MAS NMR spectra of NEt$_3$ adsorbed on (a) silica-alumina and (b) silicon dioxide.
Figure 6B:
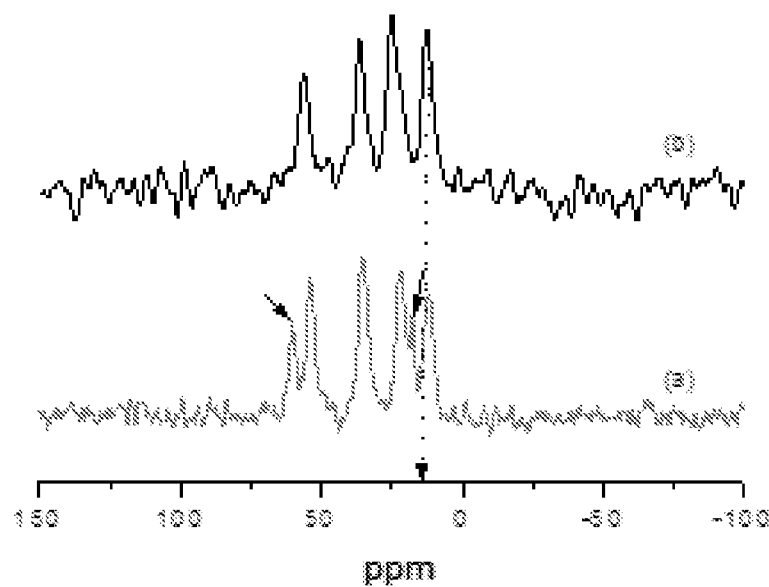
FIG. 6B depicts solid-state $^{13}$C CP MAS NMR spectra of an amine catalyst supported on (a) silica-alumina and (b) silicon dioxide. The two arrows in spectrum (a) refer to the ethoxy peaks obtained by refluxing the Si—Al sample in a solution including ethanol.
Figure 6C:
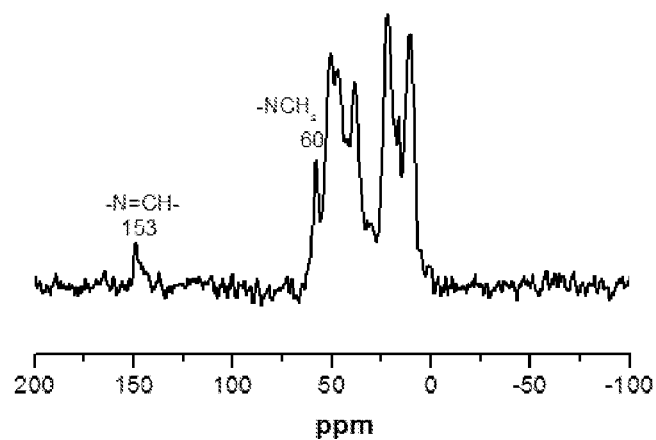
FIG. 6C depicts the solid-state $^{13}$C CP MAS NMR spectrum of an amine catalyst supported on silica-alumina following treatment with butan-2-one.

The Si—Al supported amine catalyst was characterized by in situ FT-IR spectroscopy using butan-2-one as a probe molecule. The spectrum recorded at 298 K over Si—Al—NEt-NH$_2$ catalyst showed a band at 1700 cm$^{-1}$ followed by the formation of a strong band at 1660 cm$^{-1}$ and a weak band at 1650 cm$^{-1}$. The 1700 cm$^{-1}$ peak is related to the adsorption of methyl ketone on the Si—(OH)—Al groups and showed ~15 cm$^{-1}$ downfield shift in carbonyl peaks from gas phase while the sharp peak observed at 1660 cm$^{-1}$ can be assigned to the formation of imine (—HC=N—) species. $^{13}$C CP MAS NMR spectrum of Si—Al—NEtNH$_2$ sample after treatment with butan-2-one showed a peak at δ=160 ppm (—N=CH—), and at δ=63 ppm (N—CH$_2$), indicating the rapid formation of imine intermediate by dehydration (FIG. 6C). The shoulder at 1650 cm$^{-1}$ can be related to the formation of iminium species and the formation of such iminium intermediates were frequently reported with homogenous secondary amine catalysts. The formation of iminium/enamine groups observed over secondary amines is in good accordance with previous reports that these catalysts may operate through an enamine mechanism.

Increasing the temperature from 298 K to 473 K produced a progressive decrease in the peak at 1700 cm$^{-1}$ and the appearance of a new peak for C=C vibrations at 1585 cm$^{-1}$. These observations suggest that enamines may interact with the adsorbed methyl ketones to produce the dimerized ketone product. To investigate this observation, in a separate experiment, in situ IR spectra of Si—Al—NEtNH$_2$ catalyst were acquired by first saturating the sample with pyridine prior to exposure of the catalyst to butan-2-one. Saturation of the sample with the pyridine prior to the addition of butan-2-one resulted in the absence of a peak at 1700 cm$^{-1}$. This suggests that pyridine may passivate the sites where the ketone adsorbs and subsequently reacts to form C—C bond, consistent with the experimental findings. Without wishing to be bound by any theory, the IR results support the need for a combination of basic amine groups and acidic Si—(OH)—Al groups and explain why supported amines are more active than the homogenous amine catalysts.

Example 12

Figure 10A:
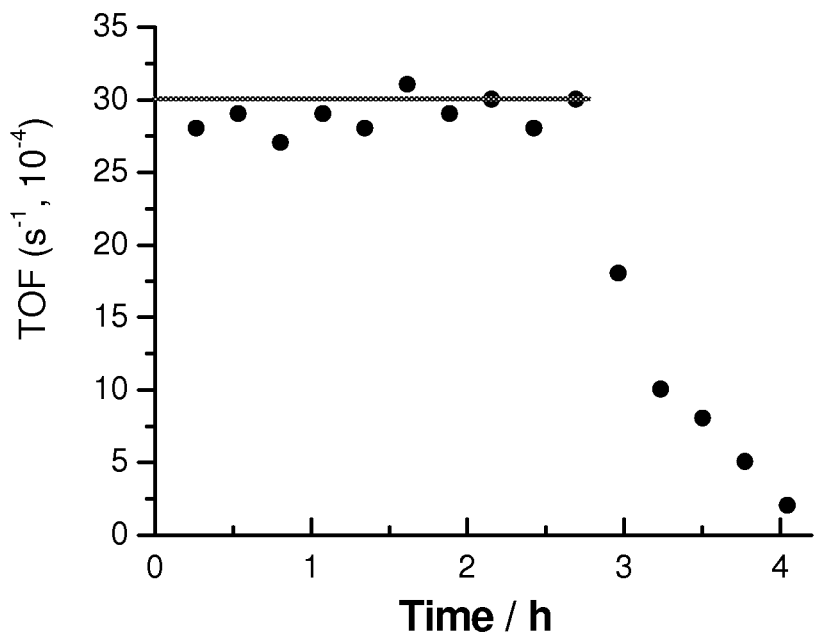
FIG. 10A depicts a graph showing Turnover Frequency (TOF) over time of an amine catalyst supported on silica-alumina when butanoic acid is added at 3 h.
Figure 10B:
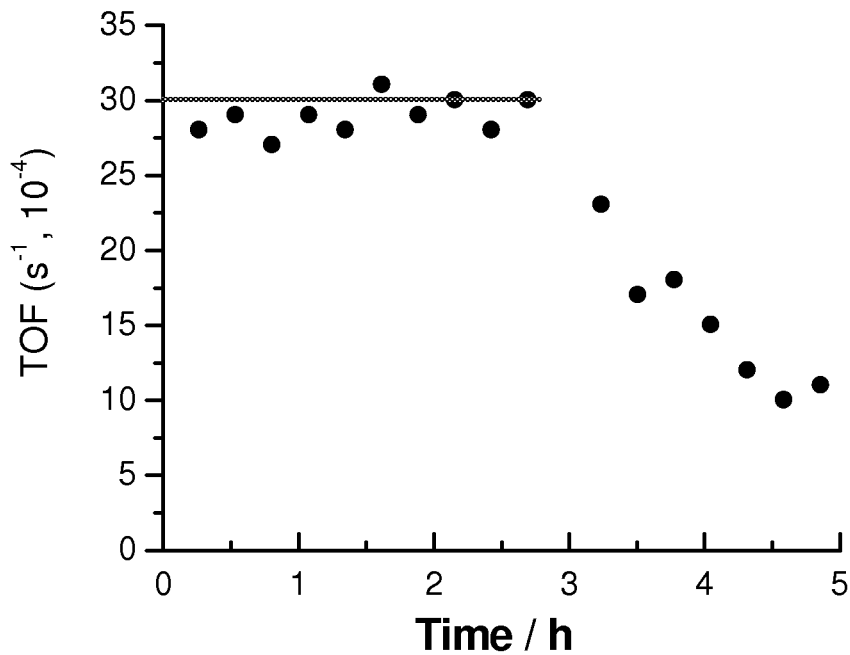
FIG. 10B depicts a graph showing TOF over time of an amine catalyst supported on silica-alumina when 2,6-di-tert-butyl pyridine is added at 3 h.

The Effect of Unsupported Acid or Base Addition on Supported Amine Catalyst Activity This Example demonstrates how the activity a Si—Al supported amine catalyst in a dimerization reaction is affected by co-feeding an unsupported acid or base into the reaction mixture. The catalyst used was Si—Al—NEt-NH$_2$, as listed in Table 1, prepared as described in Experiment 1. The dimerization of butan-2-one was carried out as described in Example 5, with $P_{total}$=1 atm; $P_{butan}$-2-one=0.2 kPa, balance He; total gas flow rate=150 cm$^3$min$^{-1}$; T=423 K. In one experiment, butanoic acid was introduced into the butan-2-one feed at t=3 h and at a pressure of 0.1 kPa. In another experiment, 2,6-di-tert-butyl pyridine was into the butan-2-one feed at t=3 h and at a pressure of 0.1 kPa. FIG. 10A depicts a graph of the Turnover Frequency (TOF) of the catalyst over time when butanoic acid is added at 3 h. FIG. 10B depicts a graph of the TOF of the catalyst over time when 2,6-ditertiarybutyl pyridine is added at 3 h.

Poisoning experiments were conducted to identify the role of acidic groups on the amine grafted Si—Al sample. Co-feeding butanoic acid into the butan-2-one reaction stream drastically decreased the catalyst activity. This result is consistent with the reaction studies listed in Table 3, which showed that combining amines with organic acids decreases catalytic activity. Co-feeding 2,6-di-tert-butyl pyridine, which can selectively titrate the Brønsted-acid sites of silica-alumina, progressively decreased the activity, the activity becoming negligible after 3 h time on stream. Without wishing to be bound by any theory, the observed decrease in catalytic activity demonstrates that acidic sites (Al—(OH)—Si) may play an important role in enhancing the catalytic activity of the Si—Al supported amine catalyst and that acid and base groups may work cooperatively.

Example 13

$^{13}$C CP MAS NMR Study of Supported and Adsorbed Amine Catalysts

This Example demonstrates the differences between the $^{13}$C CP MAS NMR spectra of an amine catalyst supported by Si—Al or silica, and an amine catalyst adsorbed onto Si—Al or silica.

The Si—Al supported catalyst used was Si—Al—NHR, as listed in Table 1, prepared as described in Experiment 1. The silica (SiO$_2$) supported catalyst used was SiO$_2$—NHR, prepared in as described in Experiment 1 using silica instead of silica-alumina as the solid support. The adsorbed amine catalysts used were triethylamine adsorbed on Si—Al or SiO$_2$, and were prepared by an impregnation procedure. To 1 g of SiO$_2$ or Si—Al support, 0.11 g (1 mmol) of triethylamine was added dropwise. The sample was mixed and dried in a vacuum oven at 323 K for 3 h, to provide the triethylamine adsorbed on Si—Al or SiO$_2$. The $^{13}$C CP MAS NMR spectra of the supported amine catalysts is shown in FIG. 6A. The $^{13}$C CP MAS NMR spectra of the adsorbed amine catalysts is shown in FIG. 6B.

To 1 g of SiO$_2$ or Si—Al support, 0.11 g (1 mmol) of triethyl amine was added dropwise. The sample was then mixed well and dried in a vaccum oven at 50° C. for 3 h, before used for the NMR analysis.

The $^{13}$C CP MAS NMR spectra of triethylamine adsorbed onto Si—Al showed a strong upfield shift in the terminal carbon position, compared to triethylamine adsorbed onto SiO$_2$. The $^{13}$C CP MAS NMR spectra of the Si—Al—NHR sample showed similar peak positions to that in SiO$_2$—NHR, indicating the absence of strong interaction between the Brønsted acid sites and the supported amine groups.

Example 14

Dimerization Selectivity of a Si—Al Supported Amine Catalyst as Compared to a Hydrotalcite Catalyst in the Dimerization of Butan-2-one Supported Amine Catalyst Study:
The Si—Al supported catalyst used was Si—Al—NEt-NH$_2$, as listed in Table 1, prepared as described in Experiment 1. Self-condensation of butan-2-one was performed using 100 mg of supported amine catalyst and 2 mmol of butan-2-one, at 473 K.

Hydrotalcite Catalyst Study:
Hydrotalcite was purchased from Sigma-Aldrich and calcined at 823 K for 5 h before use. Self-condensation of butan-2-one was performed following the procedure set forth for the supported amine catalyst study above, using 50 mg of hydrotalcite as the catalyst.

Results showed that the selectivity for dimer product was greater for the supported amine catalyst than the HT catalyst. The supported amine catalyst (Si—Al—NEt-NH$_2$) showed a dimer selectivity of 96% and a trimer selectivity of 4%, whereas HT showed a dimer selectivity of 32% and a trimer selectivity of 68%.

What is claimed:

1. A method of producing an α,β-unsaturated ketone, comprising:
    contacting a methyl ketone of Formula (A) with an amine catalyst; and
    producing an α,β-unsaturated ketone from at least a portion of the methyl ketone by a condensation reaction, wherein:
  the methyl ketone of Formula (A) is:

(A)

wherein:
    R$^1$ is H, alkyl, carbocyclyl, or heterocyclyl;
      wherein the alkyl, carbocyclyl, or heterocyclyl is unsubstituted or substituted with one or more substituents independently selected from the group consisting of hydroxyl, nitro, and halo; and
    x is an integer greater than or equal to 1, and
  the amine catalyst comprises an amine moiety, a solid support, and a linker, wherein the linker attaches the amine moiety to the solid support, and wherein the solid support comprises silica, alumina, silica-alumina, TiO$_2$, ZrO$_2$, or Nb$_2$O$_5$, or any combinations thereof.

2. The method of claim 1, wherein the α,β-unsaturated ketone is a compound of Formula (L):

(L)

or any isomers thereof, wherein R$^1$ and x are as defined for Formula (A).

3. The method of claim 2, wherein the methyl ketone is contacted with the amine catalyst in the presence of water.

4. The method of claim 2, wherein the α,β-unsaturated ketone of Formula (L), or any isomers thereof, is produced with a yield of at least 10% at a weight hourly space velocity of about 0.2 grams of ketone of Formula (A) per gram of catalyst per hour.

5. The method of claim 1, further comprising contacting a composition comprising biomass or sugars with a fermentation host to produce a fermentation product mixture, wherein the fermentation product mixture comprises the methyl ketone of Formula (A).

6. The method of claim 1, wherein the amine moiety comprises:

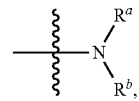

wherein R$^a$ and R$^b$ at each occurrence are independently H, alkyl, carbocyclyl, heterocyclyl, or ether, or any combinations thereof;

wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;

or $R^a$ and $R^b$ are taken together with the nitrogen atom to which they are both attached to form a heterocycle, wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.

7. The method of claim 1, wherein the amine moiety comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

8. The method of claim 1, wherein the solid support is porous.

9. The method of claim 1, wherein the solid support comprises a plurality of pores, wherein at least a portion of the pores have a pore diameter between 2 nm and 50 nm.

10. The method of claim 1, wherein the solid support comprises an acid moiety.

11. The method of claim 1, wherein the linker comprises: alkyl, -aliphatic-, -aryl-, -carbocycle-, -heterocycle-, -sulfone-, or -ether-, or any combinations thereof;
wherein the -alkyl-, -aliphatic-, -aryl-, -carbocycle-, -heterocycle-, -sulfone-, -ether- are unsubstituted or substituted with one or more substituents independently selected from the group consisting of alkyl, hydroxyl, amine, oxo, carboxyl, imine, carbocyclyl, and heterocyclyl.

12. The method of claim 1, wherein the linker comprises at least three linear chain atoms.

13. The method of claim 1, wherein the amine moiety is a secondary amine.

14. The method of claim 1, wherein the methyl ketone is contacted with the amine catalyst in the presence of an acid.

15. The method of claim 14, wherein the acid is supported or unsupported.

16. The method of claim 1, wherein the methyl ketone of Formula (A) is provided in a fermentation product mixture.

17. A method, comprising:
producing an α,β-unsaturated ketone according to the method of claim 1; and
hydrodeoxygenating the α,β-unsaturated ketone to produce an alkane.

18. A method, comprising:
producing an α,β-unsaturated ketone according to the method of claim 1; and
reducing the α,β-unsaturated ketone to produce an alcohol.

19. The method of claim 1, wherein the solid support comprises silica.

20. The method of claim 1, wherein the solid support comprises alumina.

21. The method of claim 1, wherein the solid support comprises silica-alumina.

22. The method of claim 1, wherein the solid support comprises $TiO_2$.

23. The method of claim 1, wherein the solid support comprises $ZrO_2$.

24. The method of claim 1, wherein the solid support comprises $Nb_2O_5$.

* * * * *